United States Patent
Dubin et al.

(10) Patent No.: US 6,548,270 B1
(45) Date of Patent: Apr. 15, 2003

(54) DNA ENCODING HUMAN ACID-SENSING ION CHANNEL BNAC4 (ASIC4)

(75) Inventors: Adrienne Elizabeth Dubin, San Diego, CA (US); Jayashree Pyati, San Diego, CA (US); Rene Huvar, Santee, CA (US); Mark G. Erlander, Encinitas, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/518,959

(22) Filed: Mar. 3, 2000

(51) Int. Cl.⁷ .......................... C12N 15/12; C12N 5/00; C12N 15/63; C07H 21/04; C07K 14/00

(52) U.S. Cl. ................... 435/69.1; 435/325; 435/320.1; 536/23.5; 530/350

(58) Field of Search ................................ 435/69.1, 325, 435/320.1; 536/23.5; 530/350

(56) References Cited

U.S. PATENT DOCUMENTS 5,892,018 A   4/1999   Welsh et al. ................ 536/23.5

FOREIGN PATENT DOCUMENTS

| EP | 0875570 A2 | * | 4/1998 |
| EP | 0 875 570 A2 | | 11/1998 |
| WO | WO 99/21981 | | 5/1999 |
| WO | WO 99/63081 | | 12/1999 |
| WO | WO 9963081 A2 | * | 12/1999 |

OTHER PUBLICATIONS

Mikayama T. Molecular cloning and functional expression of a cDNA encoding glycosylation–inhibiting factor. Proc. Natl. Acad. Sci. USA vol. 90, pp. 10056–10060, 1993.*

Voet et al. Biochemistry. 1990. John Wiley & Sons, Inc.. pp. 126–128 and 228–234.*

Babinski, Kazimierz; Le, Khanh–Tuoc; Seguela, Phillipe. Molecular Cloning and Regional Distribution of a Human Proton Receptor Subunit with Biphasic Functional Properties. Journal of Neurochemistry, 1999.

Bassilana, Frederic; Champigny, Guy; Waldmann, Rainer; de Weille, Jan R.; Heurteaux, Catherine; Lazdunski, Michel. The Acid–sensitive Ionic Channel Subunit ASIC and the Mammalian Degenerin MDEG Form a Heteromultimeric $H^+$–gated $Na^+$ Channel with Novel Properties. The Journal of Biological Chemistry, vol. 272, No. 46, Issue of November 14, pp. 28819–28822, 1997.

Benson, Christopher J.; Eckert, Stephani P.; McCleskey, Edwin W. Acid–Evoked Currents in Cardiac Sensory Neurons—A Possible Mediator of Myocardial Ischemic Sensation. American Heart Association, Inc. 1999.

Bevan, Stuart; Yeats, Jan. Protons Activate A Cation Conductance In A Sub–Population Of Rat Dorsal Root Ganglion Neurones. Journal of Physiology, 433, pp. 145–191, 1991.

Canessa, Cecilia M. What Is New About the Structure of the Epithelial $Na^+$ Channel? News In Physiological Sciences, vol. 11, Oct. 1996.

Chalfie, Martin; Wolinsky, Eve. The identification and suppression of inherited neurodegeneration in Caenorhabditis elegans. Nature, vol. 345, May 31, 1990.

Chen, Chih–Cheng; England, Steven; Akopian, Armen N.; Wood, John N. A sensory neuron–specific, proton–gated ion channel. Proc. Natl. Acad. Sci. USA, vol. 95, pp. 10240–10245, Aug. 1998.

Coscoy, Sylvie; de Weille, Jan R.; Lingueglia, Eric; Lazdunski, Michel. The Pre–transmembrane 1 Domain of Acid–sensing Ion Channels Participates in the Ion Pore. The Journal of Biological Chemistry, vol. 274, No. 15, Issue of Apr. 9, pp. 10129–10132, 1999.

De Weille, Jan. R.: Bassilana, Frederic; Lazdunski Michael Waldmann, Rainer. Identification, functional expression and chromosomal localisation of a sustained human proton–gated cation channel. FEBS Letters 433 257–260 (1998).

Driscoll, Monica; Chalfie, Martin. The mec–4 gene is a member of a family of Caenorhabditis elegans genes that can mutate to induce neuronal degeneration. Nature, vol. 349, Feb. 14, 1991.

Garcia–Anoveros, Jaime; Derfler, Bruce; Neville–Golden, Janine; Hyman, Bradley T.; Corey, David P. BnaCl and BnaC2 constitute a new family of human neuronal sodium channels related to degenerins and epithelial sodium channels. Proc. Natl. Acad. Sci. USA, vol. 94, pp. 1459–1464, Feb., 1997.

Garcia–Anoverso, Jaime; Garcia, Jesus A.; Liu, Jing–Dong; Corey, David P. The Nematode Degenerin UNC–105 Forms Ion Channels that Are Activated by Degeneration–or Hyper-contraction–Causing Mutations. Neuron, vol. 20, 1231–1241, Jun. 1998.

Garcia–Anoveros, Jaime; Ma, Charles; Chalfie, Martin. Regulation of Caenorhabditis elegans degenerin proteins by a putative extracellular domain. Current Biology, vol. 5, No. 4, 1995.

Giffard, Rona G.; Monyer, Hannelore; Christine, Chadwick W.; Choi, Dennis W. Acidois reduces NMDA receptor activation, glutamate neurotoxicity, and oxygen–glucose deprivation neuronal injury in cortical cultures. Brain Research, 506 339–342 (1990).

(List continued on next page.)

Primary Examiner—David S. Romeo
Assistant Examiner—Joseph F. Murphy
(74) Attorney, Agent, or Firm—John W. Wallen, III

(57) ABSTRACT

DNA encoding human acid sensing ion channel BnaC4 has been cloned and characterized. The recombinant protein is capable of forming biologically active protein. The cDNA's have been expressed in recombinant host cells that produce active recombinant protein. The recombinant protein is also purified from the recombinant host cells. In addition, the recombinant host cells are utilized to establish a method for identifying modulators of the receptor activity, and receptor modulators are identified.

8 Claims, 10 Drawing Sheets

OTHER PUBLICATIONS

Grantyn, Rosemarie; Lux, Hans Dieter. Similarity and mutual exclusion of NMDA– and proton–activated transient $Na^+$ –currents in rat tectal neurons. Neuroscience Letters, 89, 198–203 (1988).

Hall, David H.; Gu, Guoqiang; Garcia–Anoveros, Jaime; Gong, Lei; Chalfie, Martin; Driscoll, Monica. Neuropathology of Degenerative Cell Death in Caenorhabditis elegans. The Journal of Neuroscience, 17(3):1033–1045, Feb. 1, 1997.

Ishibashi, Kenichi; Marumo, Fumiaki. Molecular Cloning of a DEG/ENaC Sodium Channel cDNA from Human Testis. Biochemical and Biophysical Research Communications 245, 589–593 Article No. RC988483 (1998).

Kovalchuk, Yu. N.; Krishtal, O.A.; Nowycky, M.C. The proton–activated inward current of rat sensory neurons includes a calcium component. Neuroscience Letters, 115, 237–242, (1990).

Kristian, Tibor; Siesjo, Bo K. Calcium–Related Damage In Ischemia. Life Sciences, vol. 59, No. 5/6, pp. 357–367, 1996.

Leist, Marcel; Nicotera, Pierluigi. Calcium and Cell Death. Cell Death and Diseases of the Nervous System.

Li, P.–A.; Siesjo, B.K. Role of hyperglycaemia–related acidosis in ischaemic brain damage. Acta Physiol Scand 161, 567–580, 1997.

Liman, Emily R.,; Tytgat, Jan; Hess, Peter. Subunit Stoichiometry of a Mammalian $K^+$ Channel Determined by Construction of Multimeric cDNAs. Neuron, vol. 9, 861–871, Nov., 1992.

Lindahl, Olov. Pain–A General Chemical Explanation. Advances in Neurology, vol. 4, 1974.

Linqueglia, Eric; de Weille, Jan. R.; Bassilana, Frederic; Heurteaux, Catherine; Sakai, Hideki; Waldmann, Rainer; Lazdunski, Michel. The Journal of Biological Chemistry, vol. 272, No. 47, Issue of Nov. 21, pp. 29778–29783, 1997.

Mattson, Mark P. Free Radicals, Calcium, And The Synaptic Plasticity–Cell Death Continuum: Emerging Roles of The Transcription Factor NFκB. International Review of Neurobiology, vol. 42, 1998.

Olson, Timothy H., Riedl, Maureen S.; Vulchanova, Lucy; Ortiz–Gonzalez, Xilma R.; Elde$^{CA}$, Robert. An acid sensing ion channel (ASIC) localized to small primary afferent neurons in rats. NeuroReport, vol. 9, No. 6, Apr. 20, 1998.

Price, Margaret P.; Snyder, Peter M.; Welsch, Michael J. Cloning and Expression of a Novel Human Brain $Na^+$ Channel. The Journal of Biological Chemistry, vol. 271, No. 14, Issue of Apr. 5, pp. 7879–7882, 1996.

Reeh, Peter W.; Steen, Kay H. Tissue acidosis in nociception and pain. Progress in Brain Research, vol. 113.

Sontheimer, H.; Perouansky, M.; Hoope, D.; Lux, H.D.; Grantyn, R.; Kettenmann, H. Glial Cells of the Oligodendrocyte Lineage Express Proton–Activated $Na^+$ Channels. Journal of Neuroscience Research 24:495–500 (1989).

Steen, H.; Issberner, Ulrich; Reeh, Peter W. Pain due to experimental acidosis in human skin: evidence for non–adapting nociceptor excitation. Neuroscience Letters 199, 29–32 (1995).

Tominaga, Makoto, Caterina, Michael J; Rosen, Tobias A.; Julius, David. The Capsaicin Receptor: A Heat–and proton–activated Ion Channel. Department of Cellular and Molecular Pharmacology, University of California, San Francisco.

Ueno, Shinya; Nakaye, Toshio; Akaike, Norio. Proton–Induced Sodium Current In Freshly Dissociated Hypothalamic Neurones Of The Rat. Journal of Physiology, 447, pp. 309–327, 1992.

Varmin, Thomas. Proton–gated ion channels in cultured mouse cortical neurons. Neuro–Pharmacology, 38, 1875–1881, 1999.

Verkratsky, Alexej; Toescu, Emil C. Integrative Aspects of Calcium Signalling. Plenum Press, 1998.

Waldmann, Rainer; Bassilana, Frederic; de Weille, Jan; Champigny, Guy; Heurteaux, Catherine; Lazdunski, Michel. The Journal of Biological Chemistry, vol. 272, No. 34, Issue of Aug. 22, pp. 20975–20978, 1997.

Waldmann, Rainer; Champigny, Guy; Bassilana, Frederic; Heurteaux, Catherine; Lazdunski, Michel. A proton–gated cation channel involved in acid–sensing. Letters to Nature, vol. 386, Mar. 13, 1997.

Waldmann, Ranier;Champigny, Guy; Voilley, Nicholas; Lauritzen, Inger; Lazdunski, Michel. The Mammalian Degenerin MDEG, an Amiloride–sensitive Cation Channel Activated by Mutations Causing Neurodegeneration in Caenorhabditis elegans. The Journal of Biological Chemistry, vol. 271, No. 18, Issue of May 3, pp. 10433–10436, 1996.

Waldman, Ranier; Lazdunski, Michel. $H^+$ –gated cation channels: neuronal acid sensors in the NaC/DEG family of ion channels. Current Opinion in Neurobiology, 8:481–424, 1998.

* cited by examiner

FIG. 1

SEQ.ID.NO.6. Human BNAC4 nucleotide sequence of the coding sequence (1620 bp).

ATGCCGATCGAGATTGTGTGCAAAATCAAATTTGCTGAGGAGGATGCGAA
ACCCAAGGAGAAGGAGGCAGGGGATGAGCAGAGCCTCCTCGGGGCTGTTG
CCCCTGGAGCAGCCCCCCGAGACCTGGCCACCTTTGCCAGCACCAGCACC
CTGCATGGACTGGGCCGGGCCTGTGGCCCAGGCCCCCACGGACTGCGCAG
AACCCTGTGGGCACTGGCCCTACTCACCTCGCTGGCTGCCTTCCTGTACC
AGGCGGCTGGCCTGGCCCGGGGCTACCTGACCCGGCCTCACCTGGTGGCA
ATGGACCCCGCTGCCCCAGCCCAGTGGCGGGCTTCCCGGCTGTCACCCT
CTGCAATATCAACCGCTTCCGGCATTCGGCACTCAGCGATGCCGACATCT
TCCACCTGGCCAATCTGACAGGGCTGCCCCCCAAAGACCGGGATGGGCAC
CGTGCGGCTGGCCTGCGCTACCCAGAGCCTGACATGGTAGACATCCTCAA
CCGCACTGGCCACCAGCTCGCCGACATGCTTAAGAGCTGCAACTTCAGTG
GGCATCACTGCTCCGCCAGCAACTTCTCTGTGGTCTATACTCGCTATGGG
AAGTGTTACACCTTCAACGCGGACCCGCGGAGCTCGCTGCCCAGCCGGGC
AGGGGGCATGGGCAGTGGCCTGGAGATCATGCTGGACATCCAGCAGGAGG
AGTACCTGCCCATCTGGAGGGAGACAAATGAGACGTCGTTTGAGGCAGGT
ATTCGGGTGCAGATCCACAGCCAGGAGGAGCCGCCCTACATCCACCAGCT
GGGGTTCGGGGTGTCCCCAGGCTTCCAGACCTTTGTGTCCTGCCAGGAAC
AGCGGCTGACCTACCTGCCCCAGCCCTGGGGCAACTGCCGCGCAGAGAGT
GAGCTCAGGGAGCCTGAGCTTCAGGGCTACTCGGCCTACAGTGTGTCTGC
CTGCCGGCTGCGCTGTGAAAAGGAGGCCGTGCTTCAGCGCTGCCACTGCC
GGATGGTGCACATGCCAGGCAATGAGACCATCTGCCCACCAAATATCTAC
ATCGAGTGTGCAGACCACACACTGGACTCCCTGGGTGGGGCCCTGAGGG
CCCGTGCTTCTGCCCCACCCCCTGCAACCTGACACGCTATGGGAAAGAGA
TCTCCATGGTCAGGATCCCCAACAGGGGCTCAGCCCGGTACCTGGCGAGG
AAGTACAACCGCAACGAGACCTACATACGGGAGAACTTCCTGGTCCTAGA
TGTCTTCTTTGAGGCCCTGACCTCTGAAGCCATGGAGCAGCGAGCAGCCT
ATGGCCTGTCAGCCCTGCTGGGAGACCTCGGGGACAGATGGGCCTGTTC
ATTGGGGCCAGCATCCTCACGTTGCTGGAGATCCTCGACTACATCTATGA
GGTGTCCTGGGATCGACTGAAGCGGGTATGGAGGCGTCCCAAGACCCCCC
TGCGGACCTCCACTGGGGGCATCTCCACTTTGGGGCTTCAGGAGCTGAAG
GAACAGAGTCCCTGCCCGAGCCTGGGCCGAGCGGAGGGTGGGGGGGTCAG
CAGTCTGCTCCCCAATCACCACCACCCCCACGGTCCCCCAGGAGGTCTCT
TTGAAGATTTTGCTTGCTAG

Underlined codons signify keto and pyrimidine differences observed in different purified cDNAs.

FIG. 2A

SEQ.ID.NO.7. The nucleotide sequence of human BNAC4 (2528 bp) is shown including 164 bp 5' UT and 744 bp 3'UT.

ACTCCCCCACCTCGGGCCCCCACCCTGTCCCTGTCCTCTTCCCGCTTGCC
CTGAGTTTAGAAGAGCAGCCGCTGCCACCACTGCCACTCGGGAGGGCACC
AGGGCTGCTGGCTAGGGAGGGACAGGGCAGGGAGGCTCTGGCCAGTCCCA
GCAGCCGGGGACAGATGCCGATCGAGATTGTGTGCAAAATCAAATTTGCT
GAGGAGGATGCGAAACCCAAGGAGAAGGAGGCAGGGGATGAGCAGAGCCT
CCTCGGGGCTGTTGCCCCTGGAGCAGCCCCCGAGACCTGGCCACCTTTG
CCAGCACCAGCACCCTGCATGGACTGGGCCGGGCCTGTGGCCCAGGCCCC
CACGGACTGCGCAGAACCCTGTGGGCACTGGCCCTACTCACCTCGCTGGC
TGCCTTCCTGTACCAGGCGGCTGGCCTGGCCCGGGGCTACCTGACCCGGC
CTCACCTGGTGGCAATGGACCCCGCTGCCCAGCCCCAGTGGCGGGCTTC
CCGGCTGTCACCCTCTGCAATATCAACCGCTTCCGGCATTCGGCACTCAG
CGATGCCGACATCTTCCACCTGGCCAATCTGACAGGGCTGCCCCCCAAAG
ACCGGGATGGGCACCGTGCGGCTGGCCTGCGCTACCCAGAGCCTGACATG
GTAGACATCCTCAACCGCACTGGCCACCAGCTCGCCGACATGCTTAAGAG
CTGCAACTTCAGTGGGCATCACTGCTCCGCCAGCAACTTCTCTGTGGTCT
ATACTCGCTATGGGAAGTGTTACACCTTCAACGCGGACCCGCGGAGCTCG
CTGCCCAGCCGGGCAGGGGGCATGGGCAGTGGCCTGGAGATCATGCTGGA
CATCCAGCAGGAGGAGTACCTGCCCATCTGGAGGGAGACAAATGAGACGT
CGTTTGAGGCAGGTATTCGGGTGCAGATCCACAGCCAGGAGGAGCCGCCC
TACATCCACCAGCTGGGGTTCGGGGTGTCCCCAGGCTTCCAGACCTTTGT
GTCCTGCCAGGAACAGCGGCTGACCTACCTGCCCCAGCCCTGGGGCAACT
GCCGCGCAGAGAGTGAGCTCAGGGAGCCTGAGCTTCAGGGCTACTCGGCC
TACAGTGTGTCTGCCTGCCGGCTGCGCTGTGAAAAGGAGGCCGTGCTTCA
GCGCTGCCACTGCCGGATGGTGCACATGCCAGGCAATGAGACCATCTGCC
CACCAAATATCTACATCGAGTGTGCAGACCACACACTGGACTCCCTGGGT
GGGGGCCCTGAGGGCCCGTGCTTCTGCCCCACCCCCTGCAACCTGACACG
CTATGGGAAAGAGATCTCCATGGTCAGGATCCCCAACAGGGGCTCAGCCC
GGTACCTGGCGAGGAAGTACAACCGCAACGAGACCTACATACGGGAGAAC
TTCCTGGTCCTAGATGTCTTCTTTGAGGCCCTGACCTCTGAAGCCATGGA
GCAGCGAGCAGCCTATGGCCTGTCAGCCCTGCTGGGAGACCTCGGGGGAC
AGATGGGCCTGTTCATTGGGGCCAGCATCCTCACGTTGCTGGAGATCCTC
GACTACATCTATGAGGTGTCCTGGATCGACTGAAGCGGGTATGGAGGCG
TCCAAGACCCCCTGCGGACCTCCACTGGGGGCATCTCCACTTTGGGGC
TTCAGGAGCTGAAGGAACAGAGTCCCTGCCCGAGCCTGGCCGAGCGGAG
GGTGGGGGGTCAGCAGTCTGCTCCCAATCACCACCACCCCACGGTCC
CCCAGGAGGTCTCTTTGAAGATTTTGCTTGCTAGGACGGTGCTGTGACTG
AAAGGACCCAGGAGTCTGGGACCCCTCCTGGGATCCCCAGCACATTCTCC
TGCTCCTGGGAGAGGCCTGGGGCGGTGCTCACTGGGAGGGCCAGGACTC
AGTTCCTGCTCTCATCCTCCCCTGCCCTGATGTCAGCTGCTTTGCACAAA

Start condon and end codon are underlined.

FIG. 2B

SEQ.ID.NO.7. The nucleotide sequence of human BNAC4 (2528 bp) is shown including 164 bp 5' UT and 744 bp 3'UT.

GGTCCTTCTTGTCCACACCCCTTATCCCCAGGCTGGTGCCCCGGGAGGGC
TGGAGACCAGGCCATGGGCCCTCACGGAGAGGAAGGGAAGGAAGGAGAGG
GAGGGGGAGGATAGAGCCCATCCCAGCCGGGGAGGGGGAGCCCTCTGTAC
ATTTGTAAATATTTAGGGAAAGCCGGGTGGGGGGAGGGGATACAGATGTA
GAAGGTGGGTAGGGCTACAGGGGTGGGTGATTTAGGGACAGCCAGGGTCC
CAGCCCCAATGTCAGCAGGATAGGGAGAGCCCCAGGACTCAGGAGTGCTG
GGCTGGTCCTACTTCCTGCCCCTCTCCAGGCCCAGCTCCCCTCTTGGCAG
GGGGAGAGGATGGCCCAGCAGGCCTGGCCCAGCTCCCAGTTCCCCCTGCA
CCAGCCCCACCCCTAGAGTCCCTTCTATAGGGAGGGGGCAGGAGACCTTC
CAGACTTCGGCTGAGCTTGGAGGGTGGGAAGGGAGCCTTCTCAGTCCTCT
CTCCCTCCAGTCTGATTTTATAAAGTGCTGACGAGATTGGGAATAAAGAG
GCATAAGAAAAAAAAAAAAAAAAAAA

Start condon and end codon are underlined.

FIG. 3

SEQ.ID.NO.8. Coding sequence for human BNAC4 (539 amino acids)

MPIEIVCKIKFAEEDAKPKEKEAGDEQSLLGAVAPGAAPRDLATFASTSTL
HGLGRACGPGPHGLRRTLWALALLTSLAAFLYQAAGLARGYLTRPHLVAMD
PAAPAPVAGFPAVTLCNINRFRHSALSDADIFHLANLTGLPPKDRDGHRAA
GLRYPEPDMVDILNRTGHQLADMLKSCNFSGHHCSASNFSVVYTRYGKCYT
FNADPRSSLPSRAGGMGSGLEIMLDIQQEEYLPIWRETNETSFEAGIRVQI
HSQEEPPYIHQLGFGVSPGFQTFVSCQEQRLTYLPQPWGNCRAESELREPE
LQGYSAYSVSACRLRCEKEAVLQRCHCRMVHMPGNETICPPNIYIECADHT
LDSLGGGPEGPCFCPTPCNLTRYGKEISMVRIPNRGSARYLARKYNRNETY
IRENFLVLDVFFEALTSEAMEQRAAYGLSALLGDLGGQMGLFIGASILTLL
EILDYIYEVSWDRLKRVWRRPKTPLRTSTGGISTLGLQELKEQSPCPS*L*
GR*A*EGGGVSSLLPNHHHPHGPPGGLFEDFAC

SEQ.ID.NO.9. Coding sequence for human BNAC4 (539 amino acids)

MPIEIVCKIKFAEEDAKPKEKEAGDEQSLLGAVAPGAAPRDLATFASTSTL
HGLGRACGPGPHGLRRTLWALALLTSLAAFLYQAAGLARGYLTRPHLVAMD
PAAPAPVAGFPAVTLCNINRFRHSALSDADIFHLANLTGLPPKDRDGHRAA
GLRYPEPDMVDILNRTGHQLADMLKSCNFSGHHCSASNFSVVYTRYGKCYT
FNADPRSSLPSRAGGMGSGLEIMLDIQQEEYLPIWRETNETSFEAGIRVQI
HSQEEPPYIHQLGFGVSPGFQTFVSCQEQRLTYLPQPWGNCRAESELREPE
LQGYSAYSVSACRLRCEKEAVLQRCHCRMVHMPGNETICPPNIYIECADHT
LDSLGGGPEGPCFCPTPCNLTRYGKEISMVRIPNRGSARYLARKYNRNETY
IRENFLVLDVFFEALTSEAMEQRAAYGLSALLGDLGGQMGLFIGASILTLL
EILDYIYEVSWDRLKRVWRRPKTPLRTSTGGISTLGLQELKEQSPCPS*R*
GR*V*EGGGVSSLLPNHHHPHGPPGGLFEDFAC

Astricts offset changes between SEQ.ID.NO.:8 and SEQ.ID.NO.:9.

L to R and A to V changes with Keto and pyrimidine differences as translated from polynucleotide sequences.

FIG. 4

|  | Water-injected controls | hBNaC4 cRNA injected oocytes |
|---|---|---|
| Number of living oocytes | 144 | 23 |
| Number of dead oocytes | 18 | 160 |
| Percent Alive | 89% | 13% (* $p = 1.7 \, e \, -45$) |

Function in oocytes: Human BNaC4 is activated by low pH

Function in oocytes: Human BNaC4 is activated by low pH

FIG. 6a

Functional expression of human BNaC4 in HEK293 cells is shown: viablility of GFP-positive cells transiently transfected with hBNac4 was significantly diminished after 3-6 days.

| 3-4 days | Vector + GFP transfected HEK293 [number of coverslips] | hBNaC4 + GFP transfected HEK293 [number of coverslips] |
|---|---|---|
| Number of living GFP-expressing cells | 167 | 104 |
| Number of dead GFP-expressing cells | 30 | 66 |
| Percent Alive | 85% [5] | 61% [6] (* p < e -6) |

| 5 days | pCIneo + GFP transfected HEK293 [number of coverslips] | hBNaC4 + GFP transfected HEK293 [number of coverslips] |
|---|---|---|
| Number of living GFP-expressing cells | 174 | 60 |
| Number of dead GFP-expressing cells | 60 | 84 |
| Percent Alive | 74% [5] | 42% [6] (* p < e -9) |

| 6 days | pCIneo + GFP transfected HEK293 [number of coverslips] | hBNaC4 + GFP transfected HEK293 [number of coverslips] |
|---|---|---|
| Number of living GFP-expressing cells | 139 | 57 |
| Number of dead GFP-expressing cells | 85 | 92 |
| Percent Alive | 62% [3] | 38% [3] (* p < e -5) |

Functional expression of human BNaC4 in HEK293 cells is shown: viablility of GFP-positive cells transiently transfected with hBNac4 was significantly diminished after 3-6 days.

SEQUENCE LISTING

```
<160> NUMBER OF SEQ ID NOS: 9

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 1
aacgttgaat tcgccaccat gccgatcgag attgtgtgca aaatcaaatt              50

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 2
aacgttgcgg ccgcagcacc gtcctagcaa gcaaaatctt c                      41

<210> SEQ ID NO 3
<211> LENGTH: 20
<212> TYPE: DNA
<213> ORGANISM: Artificial Sequence
```

<220> FEATURE:
<223> OTHER INFORMATION: Description of Artificial Sequence: synthetic
      oligonucleotide

<400> SEQUENCE: 3
gcttccagac ctttgtgtcc                                                  20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 4
cagaatggtc tcattgcctg g                                                21

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 5
gagctcaggg agcctgagct tcagggctac tcggcctaca                            40

<210> SEQ ID NO 6
<211> LENGTH: 1620
<212> TYPE: DNA
<213> ORGANISM: Homo sapiens

<400> SEQUENCE: 6
atgccgatcg agattgtgtg caaaatcaaa tttgctgagg aggatgcgaa acccaaggag      60
aaggaggcag gggatgagca gagcctcctc ggggctgttg cccctggagc agccccccga     120
gacctggcca cctttgccag caccagcacc ctgcatggac tggccgggc ctgtggccca     180
ggcccccacg gactgcgcag aaccctgtgg gcactggccc tactcacctc gctggctgcc     240
ttcctgtacc aggcggctgg cctggcccgg ggctacctga cccggcctca cctggtggca     300
atggaccccg ctgccccagc cccagtggcg ggcttcccgg ctgtcaccct ctgcaatatc     360
aaccgcttcc ggcattcggc actcagcgat gccgacatct tccacctggc caatctgaca     420
gggctgcccc ccaaagaccg ggatgggcac cgtgcggctg gcctgcgcta cccagagcct     480
gacatggtag acatcctcaa ccgcactggc caccagctcg ccgacatgct taagagctgc     540
aacttcagtg ggcatcactg ctccgccagc aacttctctg tggtctatac tcgctatggg     600
aagtgttaca ccttcaacgc ggacccgcgg agctcgctgc ccagccgggc agggggcatg     660
ggcagtggcc tggagatcat gctggacatc agcaggagg agtacctgcc catctggagg     720
gagacaaatg agacgtcgtt tgaggcaggt attcgggtgc agatccacag ccaggaggag     780
ccgccctaca tccaccagct gggggttcggg gtgtcccag gcttccagac ctttgtgtcc     840
tgccaggaac agcggctgac ctacctgccc cagccctggg gcaactgccg cgcagagagt     900
gagctcaggg agcctgagct tcagggctac tcggcctaca gtgtgtctgc ctgccggctg     960
cgctgtgaaa aggaggccgt gcttcagcgc tgccactgcc ggatggtgca catgccaggc    1020
aatgagacca tctgccccacc aaatatctac atcgagtgtg cagaccacac actggactcc    1080
ctgggtgggg gccctgaggg cccgtgcttc tgccccaccc cctgcaacct gacacgctat    1140

| | |
|---|---|
| gggaaagaga tctccatggt caggatcccc aacagggct cagcccggta cctggcgagg | 1200 |
| aagtacaacc gcaacgagac ctacatacgg gagaacttcc tggtcctaga tgtcttcttt | 1260 |
| gaggccctga cctctgaagc catggagcag cgagcagcct atggcctgtc agccctgctg | 1320 |
| ggagacctcg ggggacagat gggcctgttc attgggggcca gcatcctcac gttgctggag | 1380 |
| atcctcgact acatctatga ggtgtcctgg gatcgactga agcgggtatg gaggcgtccc | 1440 |
| aagacccccc tgcggacctc cactgggggc atctccactt tggggcttca ggagctgaag | 1500 |
| gaacagagtc cctgcccgag cctgggccga gcggagggtg gggggggtcag cagtctgctc | 1560 |
| cccaatcacc accacccccca cggtcccccca ggaggtctct ttgaagattt tgcttgctag | 1620 |

<210> SEQ ID NO 7
<211> LENGTH: 2528
<212> TYPE: DNA
<213> ORGANISM: Homo sapiens

<400> SEQUENCE: 7

| | |
|---|---|
| actcccccac ctcgggccccc cacccctgtcc ctgtcctctt cccgcttgcc ctgagtttag | 60 |
| aagagcagcc gctgccacca ctgccactcg ggagggcacc agggctgctg gctagggagg | 120 |
| gacagggcag ggaggctctg gccagtccca gcagccgggg acagatgccg atcgagattg | 180 |
| tgtgcaaaat caaatttgct gaggaggatg cgaaacccaa ggagaaggag gcaggggatg | 240 |
| agcagagcct cctcggggct gttgcccctg agcagcccc ccgagacctg gccacctttg | 300 |
| ccagcaccag caccctgcat ggactgggcc gggcctgtgg cccaggcccc cacggactgc | 360 |
| gcagaaccct gtgggcactg gccctactca cctcgctggc tgccttcctg taccaggcgg | 420 |
| ctggcctggc ccggggctac ctgacccggc ctcacctggt ggcaatggac cccgctgccc | 480 |
| cagccccagt ggcgggcttc ccggctgtca ccctctgcaa tatcaaccgc ttccggcatt | 540 |
| cggcactcag cgatgccgac atcttccacc tggccaatct gacagggctg ccccccaaag | 600 |
| accgggatgg gcaccgtgcg gctggcctgc gctacccaga gcctgacatg gtagacatcc | 660 |
| tcaaccgcac tggccaccag ctcgccgaca tgcttaagag ctgcaacttc agtgggcatc | 720 |
| actgctccgc cagcaacttc tctgtggtct atactcgcta tgggaagtgt tacaccttca | 780 |
| acgcggaccc gcggagctcg ctgcccagcc gggcagggg catgggcagt ggcctggaga | 840 |
| tcatgctgga catccagcag gaggagtacc tgcccatctg gagggagaca aatgagacgt | 900 |
| cgtttgaggc aggtattcgg gtgcagatcc acagccagga ggagccgccc tacatccacc | 960 |
| agctgggggtt cggggtgtcc ccaggcttcc agacctttgt gtcctgccag gaacagcggc | 1020 |
| tgacctacct gccccagccc tggggcaact gccgcgcaga gagtgagctc agggagcctg | 1080 |
| agcttcaggg ctactcggcc tacagtgtgt ctgcctgccg gctgcgctgt gaaaaggagg | 1140 |
| ccgtgcttca gcgctgccac tgccggatgg tgcacatgcc aggcaatgag accatctgcc | 1200 |
| caccaaatat ctacatcgag tgtgcagacc acacactgga ctccctgggt gggggccctg | 1260 |
| agggccgtg cttctgcccc acccctgca acctgacacg ctatgggaaa gagatctcca | 1320 |
| tggtcaggat ccccaacagg ggctcagccc ggtacctggc gaggaagtac aaccgcaacg | 1380 |
| agacctacat acgggagaac ttcctggtcc tagatgtctt ctttgaggcc ctgacctctg | 1440 |
| aagccatgga gcagcgagca gcctatggcc tgtcagccct gctgggagac ctcggggac | 1500 |
| agatgggcct gttcattggg gccagcatcc tcacgttgct ggagatcctc gactacatct | 1560 |
| atgaggtgtc ctgggatcga ctgaagcggg tatggaggcg tcccaagacc cccctgcgga | 1620 |

-continued

```
cctccactgg gggcatctcc actttggggc ttcaggagct gaaggaacag agtccctgcc    1680
cgagcctggg ccgagcggag ggtggggggg tcagcagtct gctccccaat caccaccacc    1740
cccacggtcc cccaggaggt ctctttgaag attttgcttg ctaggacggt gctgtgactg    1800
aaaggaccca ggagtctggg acccctcctg ggatccccag cacattctcc tgctcctggg    1860
agaggcctgg gggcggtgct cactgggagg gccaggactc agttcctgct ctcatcctcc    1920
cctgccctga tgtcagctgc tttgcacaaa ggtccttctt gtccacaccc cttatcccca    1980
ggctggtgcc ccgggagggc tggagaccag gccatgggcc ctcacggaga ggaagggaag    2040
gaaggagagg gaggggggagg atagagccca tcccagccgg ggaggggag ccctctgtac    2100 atttgtaaat atttagggaa agccgggtgg ggggagggga tacagatgta aaggtgggt    2160 agggctacag gggtgggtga tttagggaca gccagggtcc cagccccaat gtcagcagga    2220
tagggagagc cccaggactc aggagtgctg ggctggtcct acttcctgcc cctctccagg    2280
cccagctccc ctcttggcag ggggagagga tggcccagca ggcctggccc agctcccagt    2340
tccccctgca ccagccccac ccctagagtc ccttctatag ggaggggca ggagaccttc    2400 cagacttcgg ctgagcttgg agggtgggaa gggagccttc tcagtcctct ctccctccag    2460 tctgattttta taaagtgctg acgagattgg gaataaagag gcataaagaa aaaaaaaaa    2520 aaaaaaaa                                                             2528
```

<210> SEQ ID NO 8
<211> LENGTH: 539
<212> TYPE: PRT
<213> ORGANISM: Homo sapiens

<400> SEQUENCE: 8

```
Met Pro Ile Glu Ile Val Cys Lys Ile Lys Phe Ala Glu Glu Asp Ala
 1               5                  10                  15

Lys Pro Lys Glu Lys Glu Ala Gly Asp Glu Gln Ser Leu Leu Gly Ala
             20                  25                  30

Val Ala Pro Gly Ala Ala Pro Arg Asp Leu Ala Thr Phe Ala Ser Thr
         35                  40                  45

Ser Thr Leu His Gly Leu Gly Arg Ala Cys Gly Pro Gly Pro His Gly
     50                  55                  60

Leu Arg Arg Thr Leu Trp Ala Leu Ala Leu Leu Thr Ser Leu Ala Ala
 65                  70                  75                  80

Phe Leu Tyr Gln Ala Ala Gly Leu Ala Arg Gly Tyr Leu Thr Arg Pro
                 85                  90                  95

His Leu Val Ala Met Asp Pro Ala Ala Pro Ala Pro Val Ala Gly Phe
            100                 105                 110

Pro Ala Val Thr Leu Cys Asn Ile Asn Arg Phe Arg His Ser Ala Leu
        115                 120                 125

Ser Asp Ala Asp Ile Phe His Leu Ala Asn Leu Thr Gly Leu Pro Pro
    130                 135                 140

Lys Asp Arg Asp Gly His Arg Ala Ala Gly Leu Arg Tyr Pro Glu Pro
145                 150                 155                 160

Asp Met Val Asp Ile Leu Asn Arg Thr Gly His Gln Leu Ala Asp Met
                165                 170                 175

Leu Lys Ser Cys Asn Phe Ser Gly His His Cys Ser Ala Ser Asn Phe
            180                 185                 190

Ser Val Val Tyr Thr Arg Tyr Gly Lys Cys Tyr Thr Phe Asn Ala Asp
        195                 200                 205
```

```
Pro Arg Ser Ser Leu Pro Ser Arg Ala Gly Gly Met Gly Ser Gly Leu
    210                 215                 220

Glu Ile Met Leu Asp Ile Gln Gln Glu Glu Tyr Leu Pro Ile Trp Arg
225                 230                 235                 240

Glu Thr Asn Glu Thr Ser Phe Glu Ala Gly Ile Arg Val Gln Ile His
                245                 250                 255

Ser Gln Glu Glu Pro Pro Tyr Ile His Gln Leu Gly Phe Gly Val Ser
                260                 265                 270

Pro Gly Phe Gln Thr Phe Val Ser Cys Gln Glu Gln Arg Leu Thr Tyr
                275                 280                 285

Leu Pro Gln Pro Trp Gly Asn Cys Arg Ala Glu Ser Glu Leu Arg Glu
    290                 295                 300

Pro Glu Leu Gln Gly Tyr Ser Ala Tyr Ser Val Ser Ala Cys Arg Leu
305                 310                 315                 320

Arg Cys Glu Lys Glu Ala Val Leu Gln Arg Cys His Cys Arg Met Val
                325                 330                 335

His Met Pro Gly Asn Glu Thr Ile Cys Pro Pro Asn Ile Tyr Ile Glu
                340                 345                 350

Cys Ala Asp His Thr Leu Asp Ser Leu Gly Gly Gly Pro Glu Gly Pro
    355                 360                 365

Cys Phe Cys Pro Thr Pro Cys Asn Leu Thr Arg Tyr Gly Lys Glu Ile
370                 375                 380

Ser Met Val Arg Ile Pro Asn Arg Gly Ser Ala Arg Tyr Leu Ala Arg
385                 390                 395                 400

Lys Tyr Asn Arg Asn Glu Thr Tyr Ile Arg Glu Asn Phe Leu Val Leu
                405                 410                 415

Asp Val Phe Phe Glu Ala Leu Thr Ser Glu Ala Met Glu Gln Arg Ala
                420                 425                 430

Ala Tyr Gly Leu Ser Ala Leu Leu Gly Asp Leu Gly Gly Gln Met Gly
                435                 440                 445

Leu Phe Ile Gly Ala Ser Ile Leu Thr Leu Leu Glu Ile Leu Asp Tyr
    450                 455                 460

Ile Tyr Glu Val Ser Trp Asp Arg Leu Lys Arg Val Trp Arg Arg Pro
465                 470                 475                 480

Lys Thr Pro Leu Arg Thr Ser Thr Gly Gly Ile Ser Thr Leu Gly Leu
                485                 490                 495

Gln Glu Leu Lys Glu Gln Ser Pro Cys Pro Ser Leu Gly Arg Ala Glu
                500                 505                 510

Gly Gly Gly Val Ser Ser Leu Leu Pro Asn His His Pro His Pro His Gly
                515                 520                 525

Pro Pro Gly Gly Leu Phe Glu Asp Phe Ala Cys
    530                 535

<210> SEQ ID NO 9
<211> LENGTH: 539
<212> TYPE: PRT
<213> ORGANISM: Homo sapiens

<400> SEQUENCE: 9

Met Pro Ile Glu Ile Val Cys Lys Ile Lys Phe Ala Glu Glu Asp Ala
1               5                   10                  15

Lys Pro Lys Glu Lys Glu Ala Gly Asp Glu Gln Ser Leu Leu Gly Ala
                20                  25                  30

Val Ala Pro Gly Ala Ala Pro Arg Asp Leu Ala Thr Phe Ala Ser Thr
            35                  40                  45
```

```
Ser Thr Leu His Gly Leu Gly Arg Ala Cys Gly Pro Gly His Gly
 50                      55                  60

Leu Arg Arg Thr Leu Trp Ala Leu Ala Leu Leu Thr Ser Leu Ala Ala
 65                      70                  75                  80

Phe Leu Tyr Gln Ala Ala Gly Leu Ala Arg Gly Tyr Leu Thr Arg Pro
                 85                      90                  95

His Leu Val Ala Met Asp Pro Ala Ala Pro Ala Pro Val Ala Gly Phe
                100                     105                 110

Pro Ala Val Thr Leu Cys Asn Ile Asn Arg Phe Arg His Ser Ala Leu
                115                     120                 125

Ser Asp Ala Asp Ile Phe His Leu Ala Asn Leu Thr Gly Leu Pro Pro
 130                     135                     140

Lys Asp Arg Asp Gly His Arg Ala Ala Gly Leu Arg Tyr Pro Glu Pro
145                     150                     155                 160

Asp Met Val Asp Ile Leu Asn Arg Thr Gly His Gln Leu Ala Asp Met
                165                     170                 175

Leu Lys Ser Cys Asn Phe Ser Gly His His Cys Ser Ala Ser Asn Phe
                180                     185                 190

Ser Val Val Tyr Thr Arg Tyr Gly Lys Cys Tyr Thr Phe Asn Ala Asp
            195                     200                 205

Pro Arg Ser Ser Leu Pro Ser Arg Ala Gly Met Gly Ser Gly Leu
            210                     215                 220

Glu Ile Met Leu Asp Ile Gln Gln Glu Tyr Leu Pro Ile Trp Arg
225                     230                     235                 240

Glu Thr Asn Glu Thr Ser Phe Glu Ala Gly Ile Arg Val Gln Ile His
                245                     250                 255

Ser Gln Glu Glu Pro Pro Tyr Ile His Gln Leu Gly Phe Gly Val Ser
                260                     265                 270

Pro Gly Phe Gln Thr Phe Val Ser Cys Gln Glu Gln Arg Leu Thr Tyr
            275                     280                     285

Leu Pro Gln Pro Trp Gly Asn Cys Arg Ala Glu Ser Glu Leu Arg Glu
 290                     295                     300

Pro Glu Leu Gln Gly Tyr Ser Ala Tyr Ser Val Ser Ala Cys Arg Leu
305                     310                     315                 320

Arg Cys Glu Lys Glu Ala Val Leu Gln Arg Cys His Cys Arg Met Val
                325                     330                 335

His Met Pro Gly Asn Glu Thr Ile Cys Pro Pro Asn Ile Tyr Ile Glu
                340                     345                 350

Cys Ala Asp His Thr Leu Asp Ser Leu Gly Gly Gly Pro Glu Gly Pro
            355                     360                 365

Cys Phe Cys Pro Thr Pro Cys Asn Leu Thr Arg Tyr Gly Lys Glu Ile
 370                     375                     380

Ser Met Val Arg Ile Pro Asn Arg Gly Ser Ala Arg Tyr Leu Ala Arg
385                     390                     395                 400

Lys Tyr Asn Arg Asn Glu Thr Tyr Ile Arg Glu Asn Phe Leu Val Leu
                405                     410                 415

Asp Val Phe Phe Glu Ala Leu Thr Ser Glu Ala Met Glu Gln Arg Ala
            420                     425                     430

Ala Tyr Gly Leu Ser Ala Leu Leu Gly Asp Leu Gly Gly Gln Met Gly
            435                     440                 445

Leu Phe Ile Gly Ala Ser Ile Leu Thr Leu Leu Glu Ile Leu Asp Tyr
 450                     455                     460
```

-continued

```
Ile Tyr Glu Val Ser Trp Asp Arg Leu Lys Arg Val Trp Arg Arg Pro
465             470                 475                 480

Lys Thr Pro Leu Arg Thr Ser Thr Gly Gly Ile Ser Thr Leu Gly Leu
                485                 490                 495

Gln Glu Leu Lys Glu Gln Ser Pro Cys Pro Ser Arg Gly Arg Val Glu
                500             505                 510

Gly Gly Gly Val Ser Ser Leu Leu Pro Asn His His His Pro His Gly
            515             520             525

Pro Pro Gly Gly Leu Phe Glu Asp Phe Ala Cys
        530             535
```

DNA ENCODING HUMAN ACID-SENSING ION CHANNEL BNAC4 (ASIC4)

BACKGROUND OF THE INVENTION

Tissue acidosis (increased concentrations of extracellular protons or decreased pH) is associated with a number of painful physiological (e.g., cramps) and pathological (e.g., intermittent claudication, inflammation, ischemia, myocardial infarction). The extracellular pH may decrease by more than 2 log units during tissue acidosis (Reeh and Steen, 1996). The chemoreception of acid (protons) plays a critical role in the detection of nociceptive pH imbalances that occur in a number of conditions including camps, trauma, inflammation and hypoxia (Lindahl, 1974). Local tissue acidosis (increases in extracellular $H^+$ concentration) arises from changes in the extracellular space during inflammatory or ischaemic conditions (Wall and Melzack, 1994). External acidification is a major factor in pain associated with inflammation, hematomas, cardiac or muscle ischemia, or cancer. Noxious chemical stimuli excite peripheral nerve endings of small diameter sensory neurons (nociceptors) in sensory ganglia (eg., dorsal root, nodose and trigeminal ganglia) and initiate signals that are perceived as pain. For instance, there is evidence that the sensation of pain parallels pH decreases (Steen et al., 1995). Prolonged intradermal infusion of low pH solutions can cause sensations that are similar to that felt during hyperalgesia, or chronic pain. Acid evoked currents in cardiac sensory neurons may mediate the sensation of myocardial ischemia (Benson et al., 1999). While decreasing the pH may cause a myriad of effects through a variety of mechanisms, the existence of ion channels that are directly gated (activated) by protons provides a means to pharmacologically manipulate specific pathways. A number of conductances in sensory and central neurons have been shown to be gated by low pH (Bevan and Yeats, 1991; Varming, 1999). Proton-gated cation channels with different pH sensitivities and kinetics were reported in sensory (trigeminal, cardiac and DRG) neurons (Benson et al., 1999; Bevan and Yeats, 1991; Kovalchuk et al., 1990; Krishtal and Pidoplichko, 1981), in neurons of the central nervous system (Grantyn and Lux, 1988; Ueno et al., 1992) and in oligodendrocytes (Sontheimer et al., 1989). The native proton-gated currents in DRG appear to vary among cells and include rapidly inactivating, non-inactivating and biphasic (both rapidly inactivating and subsequent non-inactivating) currents. A number of proton-gated channels have been cloned since 1996 and include the VR1 capsaicin-activated receptor (Tominaga et al., 1999) and a family of receptors that have homology to the nematode degenerin/mammalian amiloride-sensitive sodium channels (epithelial or brain Na channels; ENaC or BNaC). At least 4 of the latter have been shown to be expressed in sensory ganglia (see TABLE), suggesting a molecular correlate to the diversity of observed currents.

The cloned acid-sensing ion channels (ASICs) are structurally related to the Caenorhabditis elegans degenerins and mammalian epithelial sodium channels and are composed of 2 putative transmembrane domains and a large extracellular domain. The first member of this superfamily was the *C. elegans* deg-1 gene. A gain of function mutation of this gene (ie., the gene product was more active than wildtype) induced neuronal swellinng and degeneration (Chalfie and Wolinsky, 1990). This gene as well as a gene encoding a related protein MEC-4 (Driscoll and Chalfie, 1991) were called "degenerins" since they could mutate to toxic forms. There is a functional diversity of channels in this superfamily from H+ activated (ASICs), constitutively active (ENaC, Epithelial Na channel), peptide-gated (FMRF-receptor) in the snail to possibly stretch activation (degenerins of *C. elegans*). However, all of these family members appear to be sensitive to amiloride, are permeable to Na+, and are voltage insensitive (Waldmann and Lazdunski, 1998). With the exception of ASIC2b, all ASIC subunits form functional homomers when expressed in heterologous expression systems.

TABLE 1

| Name | Alternate name | pH 0.5 | Vrev (mV) | Genbank (species) | References |
|---|---|---|---|---|---|
| ASIC1 (2 splice variants, A and B) | BNaC2 | 6.2 (Waldmann et al., 1997) 5.9 (Chen et al., 1998) | +25 (Ena = 73) (Chen et al., 1998) | U78180, U78181 (human); U94403 (rat) | (Chen et al., 1998; Garcia Anoveros et al., 1997; Waldmann et al., 1997) (Chen et al., 1998) |
| ASIC2a | BNC1; MDEG; MDEG | 4.05 | Highly selective for Na+ (Pna:PK:Pca = 20:10:1) | U50352 (human); U53211 (rat) | (Price et al., 1996; Waldmann et al., 1996; Welsh and Price, 1999; Welsh and Price,) |
| ASIC2b* | MDEG2 | na | | Y14635 (rat); Y14634 (mouse) | (Lingueglia et al., 1997) |
| hASIC3++ | | 3.66 (fast); 3.82 (sustained) [Seguela]; 6.2; 4.3 (DeWeille et al., 1998) | +33; +48 | AF095897, AF057711, AB010575 (human) | (Babinski et al., 1999; de Weille et al., 1998; Ishibashi and Marumo, 1998; Seguela and Babinski, 1999) |
| ASIC3 | BNaC3; DRASIC | 6.5 (fast); 3.5 (sustained) | +32; +32 | AF013598 (rat) | (Waldmann et al., 1997) | pH 0.5 is the pH at which the induced current is half maximally activated.
*Splice variant of ASIC2 in rat; does not appear to form functional homomeric channels. There is no evidence for the existence of this splice variant in humans (BLAST search of EST databases).
++This may not be the ortholog of the rat ASIC3 since it is only 83% identical compared to >97% identity between rat and human ASIC1 and rat and human ASIC2.

The kinetic properties of the homomeric channels vary. ASIC1 activates and desensitizes in the continued presence of acid and thus induces only a transient response (Waldmann et al., 1997). ASIC2 activates and inactivates more slowly than ASIC1 (Bassilana et al., 1997). DRASIC produces a biphasic response to extracellular acidification (Babinski et al., 1999; Waldmann et al., 1997). The sensitivity to acid depends on the subunit (see TABLE 1) and the pH producing the half-maximal current varies from about 6.5 to near 3.

Members of the degenerin superfamily form heteromers. This has been clearly shown with the ENaC family (Canessa, 1996; Fyfe and Canessa, 1998). ASIC subunits also appear to form heteromers. ASIC subunits may co-localize. At a tissue level, ASIC1A, ASIC2a and b, and ASIC3 mRNA are expressed the brain and ASIC1A and B, ASIC2b and ASIC3 mRNA are expressed in DRG (TABLE 2). For instance, ASIC2 and ASIC1 are co-expressed in almost all regions of mouse and human brain (Garcia Anoveros et al., 1997). Immunocytochemistry using polyclonal antisera against rat ASIC1 reveals ASIC1 protein in superficial dorsal horn, DRG and spinal trigeminal nucleus and peripheral nerve fibers (Olson et al., 1998). Functional co-expression of multiple ASIC subunits reveal channels with properties that differ from either homomeric channel, particularly in terms of the pH0.5, relative ion permabilities, and kinetics (Bassilana et al., 1997). ASIC2b is capable of modifying the kinetic and permeability properties of ASIC2a and DRASIC (Lingueglia et al., 1997). Furthermore, co-expression of ASIC family members as well as hASIC3 and the structurally similar $P_2X_2$ (Seguela and Babinski, 1999) produce receptors with properties that differ from either homomer. Messenger RNA encoding the present invention is localized to regions that express other ASIC subunits and suggest that hBNaC4 likely forms heteromers as well.

Most members of the amiloride sensitive Na channel/degenerin family appear to be highly selective for Na over K (Bassilana et al., 1997; Chen et al., 1998; Waldmann et al., 1997; Waldmann et al., 1997). The sustained component of DRASIC shifts from being largely mediated by Na to being less so in the presence of MDEG2 (Lingueglia et al., 1997). Chimers of MDEG1 and MDEG2 revealed nine amino acids in the putative N terminal cytoplasmic region adjacent to the first transmembrane region (TM1) are critically important determinants of the ion selectivity of these channels. Ile19, Phe-20 and Thr-25 appear to be particularly important since mutations in these residues discriminated poorly between Na and K (became "non-selective") (Coscoy et al., 1999). Some ASIC subunits are also permeable to Ca2+: ASIC1A (PNa/PCa~2.5 (Waldmann et al., 1997)). However, not all subunits appear to form channels that are appreciably permeable to Ca2+ ((Bassilana et al., 1997; Chen et al., 1998)).

Amiloride block varies among subunits from a $K_D$ of about 10 uM to incomplete block at 100 uM (TABLE 2). While it is generally accepted that amiloride blocks the fast transient ASIC-mediated currents, there is some controversy as to the effect of amiloride on the sustained component of DRASIC (ASIC3) (Babinski et al., 1999; Bassilana et al., 1997; Waldmann et al., 1997).

TABLE 2

| Name | Localization | Amiloride sensitivity |
| --- | --- | --- |
| ASIC1A | Brain (cerebral cortex, hippocampus, cerebellum, spinal cord), trigeminal and DRG sensory neurons, (Chen et al., 1998; Waldmann et al., 1997); protein is widely expressed (Olson et al., 1998) | $K_D$ ~10 $\mu$M |
| ASIC1B | Appears to be restricted to sensory neurons (subset of small and large DRG neurons but distinct from ASIC1A (Chen et al., 1998)) | $IC_{50}$ = 21 $\mu$M (Chen et al., 1998) |
| ASIC2a | CNS (including hippocampal neurons) (Waldmann et al., 1996) | Amiloride blocked gain of function mutant channels |
| ASIC2b* | Brain (hippocampus, cerebral cortex, cerebellum, thalamus. hypothalamus), sensory neurons (Lingueglia et al., 1997) | MDEG1 + MDEG2 completely blocked by 500 $\mu$M amiloride (Lingueglia et al., 1997) |
| hASIC3++ | Widespread distribution: brain, spinal cord, trigeminal g., DRG, lung, lymph nodes, kidney, pituitary, heart and testis | 100 $\mu$M amiloride decreased sustained current by ~30%; fast component by ~63% (Seguela and Babinski, 1999); fast only: $K_D$ = 16 $\mu$M (de Weille et al., 1998) |
| Rat ASIC3 | Sensory neurons superior cervical ganglia, spinal cord, brain stem (Chen et al., 1998); | Fast component: $K_{0.5}$ ~60 $\mu$M; slow: potentiated by amiloride (Waldmann et al., 1997) |

[Underline indicates the tissues in which BNaC4 is expressed; see FIG. 8]

Mutations in the degenerin genes encoding channels homologous to the ASICs causes neurodegeneration in *C. elegans* (Garcia-Anoveros et al., 1995). During the degeneration process, cells accumulate whorls (concentric spheres of membrane) and vacuoles, swell to several times their original diameter and often die (Hall et al., 1997). Similar mutations in the extracellular loop or second hydrophobic domain MII when introduced into MDEG1 and ASIC1 produce constitutively currents and kills cultured cells expressing the channel (Bassilana et al., 1997; Waldmann et al., 1996).

In vivo, activation of proton-gated channels would lead to cellular depolarization and influx of Ca2+ either through the channel itself or through voltage-activated calcium channels. Accumulation of intracellular Ca2+ may lead to neurodegeneration (Ghosh and Greenberg, 1995; Kristian and Siesjoe, 1996; Leist and Nicotera, 1999; Mattson, 1998; Sattler and Tymianski, 1998). Although tissue acidosis is a well established feature of cerebral ischemia, the role of acidosis in ischemic neuropathology is not understood. Previously, it had been thought to play a protective role since protons inhibit NMDA receptors (Giffard et al., 1990; Tang et al., 1990; Vyklicky et al., 1990). However, acidosis in vivo exaggerates damage due to ischemia even at a time when NMDA receptors are inhibited (Li and Siesjo, 1997; Siesjo et al., 1993).

The present invention describes the cloning and function of a novel ASIC receptor family member, BNaC4. The present invention is 97% identical at the amino acid level to rat "SPASIC" (Genbank AJ242554), and therefore is a human ortholog of the rat gene. Members of the ASIC family are believed to participate in nociception but it is likely that they play other roles as well, especially in the central nervous system.

SUMMARY OF THE INVENTION

DNA molecules encoding human brain sodium channel BNaC4 that is a member of the ASIC (acid sensing ion channel family) have been cloned and characterized. The biological and structural properties of the protein are disclosed, as is the amino acid and nucleotide sequence. The recombinant protein is useful to identify modulators of the receptor BNaC4. BNaC4 is believed to play a role in neuromodulation, neurotransmission, pain, ischemia and neurodegeneration underlying diseases including but not limited to Alzheimer's disease, Huntington's disease, amyotrophic lateral sclerosis, cerebellar ataxias and Parkinsonism. Modulators identified in the assay disclosed herein are useful as therapeutic agents, which are candidates for the treatment of ischemia, inflammatory conditions and for use as analgesics for intractable pain, complex regional pain syndromes, arthritis (e.g., rheumatoid and osteoarthritis), as well as ulcers, neurodegenerative diseases, asthma, chronic obstructive pulmonary disease, irritable bowel syndrome, and psoriasis. Uses include the treatment of central nervous system diseases, diseases of the intestinal tract, abnormal proliferation and cancer especially in the digestive system, and female gonads, ulcer, liver disease, control of viscera innervated by the dorsal root ganglia, or to diagnose or treat any disorder related to abnormal expression of the human BNaC4 polypeptides, among others. In another aspect, the invention relates to methods to identify agonists and antagonists using the materials provided by the invention, and treating conditions associated with human BNaC4 imbalance. The recombinant DNA molecules, and portions thereof, are useful for isolating homologues of the DNA molecules, identifying and isolating genomic equivalents of the DNA molecules, and identifying, detecting or isolating mutant forms of the DNA molecules.

BRIEF DESCRIPTION OF THE DRAWINGS

FIG. 1—Human BNaC4 nucleotide sequence of the coding sequence (1620 bp).

FIG. 2—The nucleotide sequence of human BNaC4 (2528 bp) is shown including 164 bp 5' UT and 744 bp 3'UT.

FIG. 3—Coding sequence for human BNaC4 (539 amino acids). Two stretches of 20–34 amino acids corresponding to potential transmembrane domains are underlined.

FIG. 4—Functional expression of BNaC4 in Xenopus oocytes is shown: viability of oocyte maintained in ND-96 with 2 $Ca^{2+}$ was significantly diminished 1–4 days after injection with 1–5 ng human BNaC4 cRNA. Data were obtained from 6 separate experiments. Dead oocytes were determined visually. Data were analyzed using Chi square analysis.

DETAILED DESCRIPTION

Figure 5A:
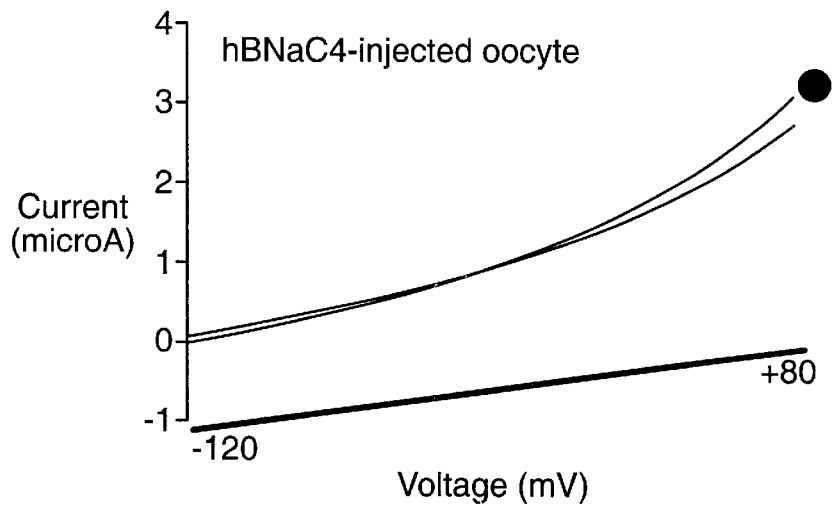
FIG. 5—Function in oocytes: Human BNaC4 is activated by low pH. a. Shown is the whole cell current activated by pH5.5 (trace labeled with black circle) which was bath applied to an oocyte 3 days after injection of 2 ng hBNaC4 cRNA. The current-voltage relationship was obtained by applying a voltage ramp from −120 to +80 mV at a rate of 0.5 mV/msec every 2 sec. Similar results were obtained from 4 sets of injected oocytes. Oocytes were constantly perfused with Ca2+ ND-96 pH 8.3. Similar responses were obtained by a pH change from pH 7.3. b. Application of low pH to a water-injected oocyte from the same experiment had no effect other than a slight reversible decrease in conductance (trace labeled with a black circle).

The present invention is drawn to a human acid sensing receptor, termed human BNaC4 for Brain sodium channel 4 (also referred to as ASIC4, acid sensing ion channel 4). The nucleotide sequence of human BNaC4 cDNA revealed a single large open reading frame of about 1620 (FIG. 1) base pairs encoding 539 (FIG. 3) amino acids. The cDNA for BNaC4 has 5' and 3'-untranslated extensions of about 164 and about 744 nucleotides, as shown in FIG. 2, wherein the 5'UTR is 1–164, the coding region is 165–1785, and the 3'UTR is 1786–2528. The first in-frame methionine was designated as the initiation codon for an open reading frame that predicts a human BNaC4 protein with an estimated molecular mass ($M_r$) of about 59,203 Da.

The predicted human BNaC4 protein was aligned with nucleotide and protein databases and are related to the acid sensing ion channel family (BNaC, ASIC). There are several conserved motifs found in this family of channel including a large putative extracellular domain (about 354 amino acids), and two predicted transmembrane domains. Thus the human BNaC4 described herein is the human homolog of the rat "SPASIC", a novel gene of the BNaC family.

Isolation of Human BNaC4 Nucleic Acid

The present invention relates to DNA encoding human BNaC4 which were isolated from human BNaC4 producing cells. Human BNaC4, as used herein, refers to protein which can specifically function as a receptor.

The complete amino acid sequence of human BNaC4 was not previously known, nor was the complete nucleotide sequence encoding human BNaC4 known. It is predicted that a wide variety of cells and cell types will contain the described human BNaC4.

Other cells and cell lines may also be suitable for use to isolate human BNaC4 cDNA. Selection of suitable cells may be done by screening for human BNaC4 activity in cell extracts or in whole cell assays, described herein. Cells that possess human BNaC4 activity in any one of these assays may be suitable for the isolation of human BNaC4 DNA or mRNA.

Any of a variety of procedures known in the art may be used to molecularly clone human BNaC4 DNA. These methods include, but are not limited to, direct functional expression of the human BNAC4 genes following the construction of a human BNAC4-containing cDNA library in an appropriate expression vector system. Another method is to screen human BNaC4-containing cDNA library constructed in a bacteriophage or plasmid shuttle vector with a labelled oligonucleotide probe designed from the amino acid sequence of the human BNAC4 subunits. An additional method consists of screening a human BNAC4-containing cDNA library constructed in a bacteriophage or plasmid shuttle vector with a partial cDNA encoding the human BNaC4 protein. This partial cDNA is obtained by the specific PCR amplification of human BNaC4 DNA fragments through the design of degenerate oligonucleotide primers from the amino acid sequence of the purified human BNaC4 protein.

Another method is to isolate RNA from human BNaC4-producing cells and translate the RNA into protein via an in vitro or an in vivo translation system. The translation of the RNA into a peptide a protein will result in the production of at least a portion of the human BNaC4 protein which can be identified by, for example, immunological reactivity with an anti-human BNaC4 antibody or by biological activity of human BNaC4 protein. In this method, pools of RNA isolated from human BNaC4-producing cells can be analyzed for the presence of an RNA that encodes at least a portion of the human BNaC4 protein. Further fractionation of the RNA pool can be done to purify the human BNaC4 RNA from non-human BNaC4 RNA. The peptide or protein produced by this method may be analyzed to provide amino acid sequences which in turn are used to provide primers for production of human BNaC4 cDNA, or the RNA used for translation can be analyzed to provide nucleotide sequences encoding human BNaC4 and produce probes for this production of human BNaC4 cDNA. This method is known in the art and can be found in, for example, Maniatis, T., Fritsch, E. F., Sambrook, J. in *Molecular Cloning: A Laboratory Manual,* Second Edition, Cold Spring Harbor Laboratory Press, Cold Spring Harbor, N.Y. 1989.

It is readily apparent to those skilled in the art that other types of libraries, as well as libraries constructed from other cells or cell types, may be useful for isolating human BNaC4-encoding DNA. Other types of libraries include, but are not limited to, cDNA libraries derived from other cells, from organisms other than human BNaC4, and genomic DNA libraries that include YAC (yeast artificial chromosome) and cosmid libraries.

It is readily apparent to those skilled in the art that suitable cDNA libraries may be prepared from cells or cell lines which have human BNaC4 activity. The selection of cells or cell lines for use in preparing a cDNA library to isolate human BNaC4 cDNA may be done by first measuring cell associated human BNAC4 activity using the measurement of human BNaC4-associated biological activity or a ligand binding assay.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual, Second Edition (Cold Spring Harbor Laboratory, Cold Spring Harbor, N.Y., 1989).

It is also readily apparent to those skilled in the art that DNA encoding human BNaC4 may also be isolated from a suitable genomic DNA library. Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual, Second Edition (Cold Spring Harbor Laboratory, Cold Spring Harbor, N.Y., 1989).

In order to clone the human BNaC4 gene by the above methods, the amino acid sequence of human BNaC4 may be necessary. To accomplish this, human BNaC4 protein may be purified and partial amino acid sequence determined by automated sequenators. It is not necessary to determine the entire amino acid sequence, but the linear sequence of two regions of 6 to 8 amino acids from the protein is determined for the production of primers for PCR amplification of a partial human BNaC4 DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the human BNaC4 sequence but will be capable of hybridizing to human BNaC4 DNA even in the presence of DNA oligonucleotides with mismatches. The mismatched DNA oligonucleotides may still sufficiently hybridize to the human BNaC4 DNA to permit identification and isolation of human BNaC4 encoding DNA. DNA isolated by these methods can be used to screen DNA libraries from a variety of cell types, from invertebrate and vertebrate sources, and to isolate homologous genes.

Purified biologically active human BNaC4 may have several different physical forms. Human BNaC4 may exist as a full-length nascent or unprocessed polypeptide, or as partially processed polypeptides or combinations of processed polypeptides. The full-length nascent human BNaC4 polypeptide may be postranslationally modified by specific proteolytic cleavage events that results in the formation of fragments of the full length nascent polypeptide. A fragment, or physical association of fragments may have the full biological activity associated with human BNaC4 however, the degree of human BNaC4 activity may vary between individual human BNaC4 fragments and physically associated human BNaC4 polypeptide fragments.

Because the genetic code is degenerate, more than one codon may be used to encode a particular amino acid, and therefore, the amino acid sequence can be encoded by any of a set of similar DNA oligonucleotides. Only one member of the set will be identical to the human BNaC4 sequence but will be capable of hybridizing to human BNaC4 DNA even in the presence of DNA oligonucleotides with mismatches under appropriate conditions. Under alternate conditions, the mismatched DNA oligonucleotides may still hybridize to the human BNaC4 DNA to permit identification and isolation of human BNaC4 encoding DNA.

DNA encoding human BNaC4 from a particular organism may be used to isolate and purify homologues of human BNaC4 from other organisms. To accomplish this, the first human BNaC4 DNA may be mixed with a sample containing DNA encoding homologues of human BNaC4 under appropriate hybridization conditions. The hybridized DNA complex may be isolated and the DNA encoding the homologous DNA may be purified therefrom.

Functional Derivatives/Variants

It is known that there is a substantial amount of redundancy in the various codons that code for specific amino acids. Therefore, this invention is also directed to those DNA sequences that contain alternative codons that code for the eventual translation of the identical amino acid. For purposes of this specification, a sequence bearing one or more replaced codons will be defined as a degenerate variation. Also included within the scope of this invention are mutations either in the DNA sequence or the translated protein, which do not substantially alter the ultimate physical properties of the expressed protein. For example, substitution of aliphatic amino acids Alanine, Valine, Leucine and Isoleucine; interchange of the hydroxyl residues Serine and Threonine, exchange of the acidic residues Aspartic acid and Glutamic acid, substitution between the amide residues Asparagine and Glutamine, exchange of the basic residues Lysine and Arginine and substitution among the aromatic residues Phenylalanine, Tyrosine may not cause a change in functionality of the polypeptide. Such substitutions are well known and are described, for instance in *Molecular Biology of the Gene*, 4th Ed. Bengamin Cummings Pub. Co. by Watson et al.

It is known that DNA sequences coding for a peptide may be altered so as to code for a peptide having properties that are different than those of the naturally occurring peptide. Methods of altering the DNA sequences include, but are not limited to site directed mutagenesis, chimeric substitution, and gene fusions. Site-directed mutagenesis is used to change one or more DNA residues that may result in a silent mutation, a conservative mutation, or a nonconservative mutation. Chimeric genes are prepared by swapping domains of similar or different genes to replace similar domains in the BNaC4 gene. Similarly, fusion genes may be prepared that add domains to the BNaC4 gene, such as an affinity tag to facilitate identification and isolation of the gene. Fusion genes may be prepared to replace regions of the BNaC4 gene, for example to create a soluble version of the protein by removing a transmembrane domain or adding a targeting sequence to redirect the normal transport of the protein, or adding new post-translational modification sequences to the BNaC4 gene. Examples of altered properties include but are not limited to changes in the affinity of an enzyme for a substrate or a receptor for a ligand. All such changes of the polynucleotide or polypeptide sequences are anticipated as useful variants of the present invention so long as the original function of the polynucleotide or polypeptide sequence of the present invention is maintained as described herein.

Identity or similarity, as known in the art, is relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity and similarity between two polynucleotide or two polypeptide sequences, both terms are well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., (1988) SIAM J. Applied Math., 48, 1073. Methods commonly employed to determine identity or similarity between sequences include, but are not limited to those disclosed in Carillo, H., and Lipman, D., (1988) SIAM J. Applied Math., 48, 1073. Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux, J., et al., (1984) Nucleic Acids Research 12(1), 387), BLASTP, BLASTN, and FASTA (Atschul, S. F. et al., (1990) J. Molec. Biol. 215, 403).

Polynucleotide(s) generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions or single-, double- and triple- stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s).

The term polypeptides, as used herein, refers to the basic chemical structure of polypeptides that is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., (1990) Meth. Enzymol. 182, 626–646 and Rattan et al., "Protein Synthesis: Posttranslational Modifications and Aging", (1992) Ann. N.Y. Acad. Sci. 663, 48–62. It will be appreciated, as is well known and as noted above, that polypeptides are not always entirely linear. For instance, polypeptides may be generally as a result of posttranslational events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in $E.$ $coli$ or other cells, prior to proteolytic processing, almost invariably will be N-formylmethionine. During post-translational modification of the peptide, a methionine residue at the NH.sub.2-terminus may be deleted. Accordingly, this invention contemplates the use of both the methionine-containing and the methionine-less amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation does not occur in bacterial hosts such as, for example, $E.$ $coli$. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having native patterns of glycosylation, inter alia. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell.

Variant(s) of polynucleotides or polypeptides, as the term is used herein, are polynucleotides or polypeptides that differ from a reference polynucleotide or polypeptide, respectively. A variant of the polynucleotide may be a naturally occurring variant such as a naturally occurring allelic variant, or it may be a variant that is not known to occur naturally. (1) A polynucleotide that differs in nucleotide sequence from another, reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed above. (2) A polypeptide that differs in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination. As used herein, a "functional derivative" of BNaC4 is a compound that possesses a biological activity (either functional or structural) that is substantially similar to the biological activity of BNaC4. The term "functional derivatives" is intended to include the "fragments," "variants," "degenerate variants," "analogs" and "homologues" or to "chemical derivatives" of BNaC4. Useful chemical derivatives of polypeptide are well known in the art and include, for example covalent modification of reactive organic site contained within the polypeptide with a secondary chemical moiety. Well known cross-linking reagents are useful to react to amino, carboxyl, or aldehyde residues to introduce, for example an affinity tag such as biotin, a fluorescent dye, or to conjugate the polypeptide to a solid phase surface (for example to create an affinity resin). The term "fragment" is meant to refer to any polypeptide subset of BNaC4. A molecule is "substantially similar" to BNaC4 if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire BNaC4 molecule or to a fragment thereof. Further particularly preferred in this regard are polynucleotides encoding variants, analogs, derivatives and fragments of SEQ ID NO.:6, and variants, analogs and derivatives of the fragments, which have the amino acid sequence of the polypeptide of SEQ ID NO.:8 or SEQ.ID.NO.:9 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the gene of SEQ ID NO.:6. Also especially preferred in this regard are conservative substitutions. Most highly preferred are polynucleotides encoding polypeptides having the amino acid sequence of SEQ ID NO.:8 or SEQ.ID.NO.:9, without substitutions.

Further preferred embodiments of the invention are polynucleotides that are at least 70% identical over their entire length to a polynucleotide encoding the polypeptide having the amino acid sequence set out in SEQ ID NO.:8 or SEQ.ID.NO.:9, and polynucleotides which are complementary to such polynucleotides. Alternatively, highly preferred are polynucleotides that comprise a region that is at least 80% identical, more highly preferred are polynucleotides at comprise a region that is at least 90% identical, and among these preferred polynucleotides, those with at least 95% are especially preferred. Furthermore, those with at least 97% identity are highly preferred among those with at least 95%, and among these those with at least 98% and at least 99% are particularly highly preferred, with at least 99% being the most preferred. The polynucleotides which hybridize to the above described polynucleotides in a preferred embodiment encode polypeptides which retain substantially the same biological function or activity as the polypeptide characterized by the deduced amino acid sequence of SEQ ID NO.:8 or SEQ.ID.NO.:9. Preferred embodiments in this respect, moreover, are polynucleotides that encode polypeptides that retain substantially the same biological function or activity as the mature polypeptide encoded by the DNA of SEQ ID NO.:6. The present invention further relates to polynucleotides that hybridize to the herein above-described sequences. In this regard, the present invention especially relates to polynucleotides that hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention may be used as a hybridization probe for RNA, cDNA and genomic DNA to isolate full-length cDNAs and genomic clones encoding the sequences of SEQ ID NO.:6 and to isolate cDNA and genomic clones of other genes that have a high sequence similarity to SEQ ID NO.:6. Such probes generally will comprise at least 15 bases. Preferably, such probes will have at least 30 bases and may have at least 50 bases. Particularly preferred probes will have at least 30 bases and will have 50 bases or less. For example, the coding region of the gene of the invention may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine to which members of the library the probe hybridizes.

The polypeptides of the present invention include the polypeptide of SEQ ID NO.:8 or SEQ.ID.NO.:9 (in particular the mature polypeptide) as well as polypeptides which have at least 70% identity to the polypeptide of SEQ ID NO.:8 or SEQ.ID.NO.:9, preferably at least 80% identity to the polypeptide of SEQ ID NO.:8 or SEQ.ID.NO.:9, and more preferably at least 90% similarity (more preferably at least 90% identity) to the polypeptide of SEQ ID NO.:8 or SEQ.ID.NO.:9 and still more preferably at least 95% similarity (still more preferably at least 95% identity) to the polypeptide of SEQ ID NO.:8 or SEQ.ID.NO.:9 and also include portions of such polypeptides with such portion of the polypeptide generally containing at least 30 amino acids and more preferably at least 50 amino acids. Representative examples of polypeptide fragments of the invention, include, for example, truncation polypeptides of SEQ ID NO.:8 or SEQ.ID.NO.:9. Truncation polypeptides include polypeptides having the amino acid sequence of SEQ ID NO.:8 or SEQ.ID.NO.:9, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Also preferred in this aspect of the invention are fragments characterized by structural or functional attributes of the polypeptide characterized by the sequences of SEQ ID NO.:8 or SEQ.ID.NO.:9. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, high antigenic index regions of the polypeptide of the invention, and combinations of such fragments. Preferred regions are those that mediate activities of the polypeptides of the invention. Most highly preferred in this regard are fragments that have a chemical, biological or other activity of the response regulator polypeptide of the invention, including those with a similar activity or an improved activity, or with a decreased undesirable activity.

Recombinant Expression of Human BNaC4

The cloned human BNaC4 DNA obtained through the methods described herein may be recombinantly expressed by molecular cloning into an expression vector containing a suitable promoter and other appropriate transcription regulatory elements, and transferred into prokaryotic or eukaryotic host cells to produce recombinant human BNaC4 protein. Techniques for such manipulations are fully described in Maniatis, T, et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including E. coli, blue-green algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids or viruses.

A variety of mammalian expression vectors may be used to express recombinant human BNaC4 in mammalian cells. Commercially available mammalian expression vectors which may be suitable for recombinant human BNaC4 expression, include but are not limited to, pMAMneo (Clontech), pcDNA3 (Invitrogen), pMC1neo (Stratagene), pXT1 (Stratagene), pSG5 (Stratagene), EBO-pSV2-neo (ATCC 37593) pBPV-1(8–2) (ATCC 37110), pdBPV-MMTneo(342–12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

A variety of bacterial expression vectors may be used to express recombinant human BNaC4 in bacterial cells. Commercially available bacterial expression vectors which may be suitable for recombinant human BNaC4 expression include, but are not limited to pET vectors (Novagen) and pQE vectors (Qiagen).

A variety of fungal cell expression vectors may be used to express recombinant human BNaC4 in fungal cells such as yeast. Commercially available fungal cell expression vectors which may be suitable for recombinant human BNaC4 expression include but are not limited to pYES2 (Invitrogen) and Pichia expression vector (Invitrogen). A variety of insect cell expression vectors may be used to express recombinant human BNaC4 in insect cells. Commercially available insect cell expression vectors which may be suitable for recombinant expression of human BNaC4 include but are not limited to pBlueBacII (Invitrogen).

DNA encoding human BNaC4 may be cloned into an expression vector for expression in a recombinant host cell. Recombinant host cells may be prokaryotic or eukaryotic, including but not limited to bacteria such as E. coli, fungal cells such as yeast, mammalian cells including but not limited to cell lines of human, bovine, porcine, monkey and rodent origin, and insect cells including but not limited to drosophila and silkworm derived cell line. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including but not limited to transformation, transfection, protoplast fusion, lipofection, and electroporation. The expression vector-containing cells are clonally propagated and individually analyzed to determine whether they produce human BNaC4 protein. Identification of human BNaC4 expressing host cell clones may be done by several means, including but not limited to immunological reactivity with anti-human BNaC4 antibodies, and the presence of host cell-associated human BNaC4 activity.

Expression of human BNaC4 DNA may also be performed using in vitro produced synthetic mRNA. Synthetic mRNA or mRNA isolated from human BNaC4 producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being generally preferred.

To determine the human BNaC4 DNA sequence that yields optimal levels of human BNAC4 activity and/or human BNaC4 protein, human BNaC4 DNA molecules including, but not limited to, the following can be constructed:

| Gene name | Start codon | End codon | total base pairs |
|---|---|---|---|
| BNaC4 | 165 | 1785 | 1620 |

(these numbers correspond to first nucleotide of first methionine and last nucleotide before the first stop codon) and several constructs containing portions of the cDNA encoding human BNaC4 protein. All constructs can be designed to contain none, all or portions of the 5' or the 3' untranslated region of human BNaC4 cDNA. Human BNaC4 activity and levels of protein expression can be determined following the introduction, both singly and in combination, of these constructs into appropriate host cells. Following determination of the human BNaC4 DNA cassette yielding optimal expression in transient assays, this human BNAC4 DNA construct is transferred to a variety of expression vectors, for expression in host cells including, but not limited to, mammalian cells, baculovirus-infected insect cells, E. coli, and the yeast S. cerevisiae.

Assay Methods for Human BNaC4

Host cell transfectants and microinjected oocytes may be used to assay both the levels of functional human BNaC4 activity and levels of total human BNaC4 protein by the following methods. In the case of recombinant host cells, this involves the co-transfection of one or possibly two or more plasmids, containing the human BNaC4 DNA encoding one or more fragments, subunits, or other functional gene. In the case of oocytes, this involves the co-injection of synthetic RNAs for human BNaC4 protein. Following an appropriate period of time to allow for expression, cellular protein is metabolically labelled with, for example $^{35}$S-methionine for 24 hours, after which cell lysates and cell culture supernatants are harvested and subjected to immunoprecipitation with polyclonal antibodies directed against the human BNAC4 protein. Alternatively, cells expressing recombinant BNaC4 are subjected to electrophysiological analysis to measure the total influx of sodium ions (Na$^+$) across the cell membrane by way of voltage differential using techniques well known by artisans in the field and described herein, including patch clamp voltage techniques as well as membrane proximal voltage sensitive dyes. Compounds that affect the proper function BNaC4 may increase or decrease the capacity to open the Na channel, may increase or decrease the rate of Na influx (thus affect the change of membrane potential), may increase or decrease the rate of desensitization or re-sensitization of the channel. Further still cells expressing constitutively functional recombinant BNaC4 diminish cellular viability, thus forming a viability based method to determine whether a test compound specifically antagonizes function of the channel. Compounds that antagonize the channel will decrease the cell death rate, and thus promote greater viability. The term "test compound" as used herein in connection with a suspected modulator of BNaC4 refers to an organic molecule that has the potential to disrupt specific ion channel activity of BNaC4. For example, but not to limit the scope of the current invention, compounds may include small organic molecules, synthetic or natural amino acid peptides, proteins, or synthetic or natural nucleic acid sequences, or any chemical derivatives of the aforementioned.

Levels of human BNaC4 protein in host cells are quantitated by immunoaffinity and/or ligand affinity techniques. Human BNaC4-specific affinity beads or human BNaC4-specific antibodies are used to isolate for example $^{35}$S-methionine labelled or unlabelled human BNaC4 protein. Labelled human BNaC4 protein is analyzed by SDS-PAGE. Unlabelled human BNaC4 protein is detected by Western blotting, ELISA or RIA assays employing human BNaC4 specific antibodies.

Other methods for detecting human BNaC4 activity involve the direct measurement of human BNaC4 activity in whole cells transfected with human BNaC4 cDNA or oocytes injected with human BNaC4 mRNA. Human BNaC4 activity is measured by specific ligand binding or biological characteristics of the host cells expressing human BNaC4 DNA. In the case of recombinant host cells expressing human BNaC4 patch voltage clamp techniques can be used to measure channel activity and quantitate human BNaC4 protein. In the case of oocytes patch clamp as well as two-electrode voltage clamp techniques can be used to measure sodium channel activity and quantitate human BNaC4 protein.

Cell Based Assays

The present invention provides a whole cell method to detect compound modulation of human BNaC4. The method comprises the steps;

1) contacting a test compound, and a cell that contains functional human BNaC4, and
2) measuring a change in the cell in response to modified human BNaC4 function by the test compound.

The amount of time necessary for cellular contact with the compound is empirically determined, for example, by running a time course with a known human BNaC4 modulator and measuring cellular changes as a function of time.

The measurement means of the method of the present invention can be further defined by comparing a cell that has been exposed to a compound to an identical cell that has not been similarly expose to the compound. Alternatively two cells, one containing functional human BNAaC4 and a second cell identical to the first, but lacking functional human BNaC4 could be both be contacted with the same compound and compared for differences between the two cells. This technique is also useful in establishing the background noise of these assays. One of average skill in the art will appreciate that these control mechanisms also allow easy selection of cellular changes that are responsive to modulation of functional human BNaC4.

The term "cell" refers to at least one cell, but includes a plurality of cells appropriate for the sensitivity of the detection method. Cells suitable for the present invention may be bacterial, yeast, or eukaryotic.

The assay methods to determine compound modulation of functional human BNaC4 can be in conventional laboratory format or adapted for high throughput. The term "high throughput" refers to an assay design that allows easy analysis of multiple samples simultaneously, and capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, that greater numbers of samples may be performed using the design of the present invention.

The cellular changes suitable for the method of the present invention comprise directly measuring changes in the function or quantity of human BNaC4, or by measuring downstream effects of human BNaC4 function, for example by measuring secondary messenger concentrations or changes in transcription or by changes in protein levels of genes that are transcriptionally influenced by human BNaC4, or by measuring phenotypic changes in the cell. Preferred measurement means include changes in the quantity of human BNaC4 protein, changes in the functional activity of human BNaC4, changes in the quantity of mRNA, changes in intracellular protein, changes in cell surface protein, or secreted protein, or changes in Ca+2, cAMP or GTP concentration. Changes in the quantity or functional activity of human BNaC4 are described herein. Changes in the levels of mRNA are detected by reverse transcription polymerase chain reaction (RT-PCR) or by differential gene expression. Immunoaffinity, ligand affinity, or enzymatic measurement quantitates BNaC4 induced changes in levels of specific proteins in host cells. Where the protein is an enzyme, the induction of protein is monitored by cleavage of a fluorogenic or calorimetric substrate.

Preferred detection means for cell surface protein include flow cytometry or statistical cell imaging. In both techniques the protein of interest is localized at the cell surface, labeled with a specific fluorescent probe, and detected via the degree of cellular fluorescence. In flow cytometry, the cells are analyzed in a solution, whereas in cellular imaging techniques, a field of cells is compared for relative fluorescence.

The present invention is also directed to methods for screening for compounds that modulate the expression of DNA or RNA encoding human BNaC4 as well as the function of human BNAC4 protein in vivo. Compounds may modulate by increasing or attenuating the expression of DNA or RNA encoding human BNaC4, or the function of human BNaC4 protein. Compounds that modulate the expression of DNA or RNA encoding human BNaC4 or the function of human BNaC4 protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents, and human BNaC4.

Purification of Human BNaC4 Protein

Following expression of human BNaC4 in a recombinant host cell, human BNaC4 protein may be recovered to provide purified human BNaC4.

Recombinant human BNaC4 may be purified from cell lysates and extracts, by various combinations of, or individual application of salt fractionation, ion exchange chromatography, size exclusion chromatography, hydroxylapatite adsorption chromatography and hydrophobic interaction chromatography, lectin chromatography, and antibody/ligand affinity chromatography.

Recombinant human BNaC4 can be separated from other cellular proteins by use of an immunoaffinity column made with monoclonal or polygonal antibodies specific for full length nascent human BNaC4, polypeptide fragments of human BNaC4 or human BNaC4 subunits. The affinity resin is then equilibrated in a suitable buffer, for example phosphate buffered saline (pH 7.3), and the cell culture supernatants or cell extracts containing human BNaC4 or human BNaC4 subunits are slowly passed through the column. The column is then washed with the buffer until the optical density ($A_{280}$) falls to background, then the protein is eluted by changing the buffer condition, such as by lowering the pH using a buffer such as 0.23 M glycine-HCl (pH 2.6). The purified human BNAC4 protein is then dialyzed against a suitable buffer such as phosphate buffered saline.

Production and Use of Antibodies that Bind to Human BNaC4

Monospecific antibodies to human BNaC4 are purified from mammalian antisera containing antibodies reactive against human BNaC4 or are prepared as monoclonal antibodies reactive with human BNaC4 using the technique originally described by Kohler and Milstein, *Nature* 256: 495–497 (1975). Immunological techniques are well known in the art and described in, for example, *Antibodies: A laboratory manual* published by Cold Spring Harbor Laboratory Press, Cold Spring Harbor, N.Y., ISBN 0879693142. Monospecific antibody as used herein is defined as a single antibody species or multiple antibody species with homogenous binding characteristics for human BNaC4. Homogenous binding as used herein refers to the ability of the antibody species to bind to a specific antigen or epitope, such as those associated with the human BNaC4, as described above. Human BNaC4 specific antibodies are raised by immunizing animals such as mice, rats, guinea pigs, rabbits, goats, horses and the like, with rabbits being preferred, with an appropriate concentration of human BNaC4 either with or without an immune adjuvant.

Preimmune serum is collected prior to the first immunization. Each animal receives between about 0.001 mg and about 1000 mg of human BNaC4 associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of human BNaC4 in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about −20° C.

Monoclonal antibodies (mAb) reactive with human BNaC4 are prepared by immunizing inbred mice, preferably Balb/c, with human BNaC4. The mice are immunized by the IP or SC route with about 0.001 mg to about 1.0 mg, preferably about 0.1 mg, of human BNaC4 in about 0.1 ml buffer or saline incorporated in an equal volume of an acceptable adjuvant, as discussed above. Freund's adjuvant is preferred, with Freund's complete adjuvant being used for the initial immunization and Freund's incomplete adjuvant used thereafter. The mice receive an initial immunization on day 0 and are rested for about 2 to about 30 weeks. Immunized mice are given one or more booster immunizations of about 0.001 to about 1.0 mg of human BNAC4 in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp2/0, with Sp2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using human BNaC4 as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973 or by the technique of limited dilution.

Monoclonal antibodies are produced in vivo by injection of pristane primed Balb/c mice, approximately 0.5 ml per mouse, with about $1 \times 10^6$ to about $6 \times 10^6$ hybridoma cells at least about 4 days after priming. Ascites fluid is collected at approximately 8–12 days after cell transfer and the monoclonal antibodies are purified by techniques known in the art.

In vitro production of anti-human BNaC4 mAb is carried out by growing the hybridoma in tissue culture media well known in the art. High density in vitro cell culture may be conducted to produce large quantities of anti-human BNaC4 mAbs using hollow fiber culture techniques, air lift reactors, roller bottle, or spinner flasks culture techniques well known in the art. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of human BNaC4 in body fluids or tissue and cell extracts.

It is readily apparent to those skilled in the art that the above described methods for producing monospecific antibodies may be utilized to produce antibodies specific for human BNaC4 polypeptide fragments, or full-length nascent human BNaC4 polypeptide, or the individual human BNaC4 subunits. Specifically, it is readily apparent to those skilled in the art that monospecific antibodies may be generated which are specific for only one human BNaC4 subunit or the fully functional human BNaC4 protein. It is also apparent to those skilled in the art that monospecific antibodies may be generated that inhibit normal function of human BNaC4 protein.

Human BNaC4 antibody affinity columns are made by adding the antibodies to a gel support such that the antibodies form covalent linkages with the gel bead support. Preferred covalent linkages are made through amine, aldehyde, or sulfhydryl residues contained on the antibody. Methods to generate aldehydes or free sulfhydryl groups on antibodies are well known in the art; amine groups are reactive with, for example, N-hydroxysuccinimide esters.

Kit Compositions Containing Human BNaC4 Specific Reagents

Kits containing human BNaC4 DNA or RNA, antibodies to human BNaC4, or human BNaC4 protein may be prepared. Such kits are used to detect DNA which hybridizes to human BNaC4 DNA or to detect the presence of human BNaC4 protein or peptide fragments in a sample. Such characterization is useful for a variety of purposes including but not limited to forensic analyses, diagnostic applications, and epidemiological studies.

This invention relates to the use of human BNaC4 polynucleotides for the use as diagnostic reagents. Detection of a mutated form of human BNaC4 gene associated with a dysfunction will provide a diagnostic tool that can add to or define a diagnosis of a disease or susceptibility to a disease which results from under-expression or over-expression of human BNaC4. Individuals carrying mutations in the human BNAC4 gene may be detected at the DNA level by a variety of techniques well known in the are, and described herein.

The DNA molecules, RNA molecules, recombinant protein and antibodies of the present invention may be used to screen and measure levels of human BNaC4 DNA, human BNaC4 RNA or human BNaC4 protein. The recombinant proteins, DNA molecules, RNA molecules and antibodies lend themselves to the formulation of kits suitable for the detection and typing of human BNaC4. Such a kit would comprise a compartmentalized carrier suitable to hold in close confinement at least one container. The carrier would further comprise reagents such as recombinant human BNaC4 protein or anti-human BNaC4 antibodies suitable for detecting human BNaC4. The carrier may also contain a means for detection such as labeled antigen or enzyme substrates or the like.

Gene Therapy

Nucleotide sequences that are complementary to the human BNaC4 encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other human BNaC4 antisense oligonucleotide mimetics. Human BNaC4 antisense molecules may be introduced into cells by microinjection, liposome encapsulation or by expression from vectors harboring the antisense sequence. Human BNaC4 antisense therapy may be particularly useful for the treatment of diseases where it is beneficial to reduce human BNaC4 activity.

Human BNaC4 gene therapy may be used to introduce human BNaC4 into the cells of target organisms. The human BNaC4 gene can be ligated into viral vectors that mediate transfer of the human BNaC4 DNA by infection of recipient host cells. Suitable viral vectors include retrovirus, adenovirus, adeno-associated virus, herpes virus, vaccinia virus, polio virus and the like. Alternatively, human BNaC4 DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo human BNaC4 gene therapy. Human BNaC4 gene therapy may be particularly useful for the treatment of diseases where it is beneficial to elevate human BNaC4 activity. Protocols for molecular methodology of gene therapy suitable for use with the human BNaC4 gene is described in *Gene Therapy Protocols*, edited by Paul D. Robbins, Human press, Totawa N.J., 1996.

Pharmaceutical Compositions

Pharmaceutically useful compositions comprising human BNaC4 DNA, human BNaC4 RNA, or human BNaC4 protein, or modulators of human BNaC4 receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of human BNaC4-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the human BNaC4 receptor or its activity while minimizing any potential toxicity. In addition, co-administration or sequential administration of other agents may be desirable.

The present invention also has the objective of providing suitable topical, oral, systemic and parenteral pharmaceutical formulations for use in the novel methods of treatment of the present invention. The compositions containing compounds or modulators identified according to this invention as the active ingredient for use in the modulation of human BNaC4 can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a human BNaC4 modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the human BNaC4 receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like. For parenteral administration, sterile suspensions and solutions are desired. Isotonic preparations, which generally contain suitable preservatives, are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacrylamidephenol, polyhydroxy-ethylaspartamidephenol, or polyethyleneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

The following examples illustrate the present invention without, however, limiting the same thereto.

EXAMPLE 1

Generation of Human Thalamus cDNA Library
cDNA Synthesis
First Strand Synthesis Approximately 5 $\mu$g of human thalamus mRNA (Clontech) was used to synthesize cDNA using the cDNA synthesis kit (Life Technologies). Two microliters of Not1 primer adapter was added to 5 $\mu$l of mRNA and the mixture was heated to 70° C. for 10 minutes and placed on ice. The following reagents were added on ice: 4 $\mu$l of 5×first strand buffer (250 mM TRIS-HCI (pH8.3), 375 mM KCl, 15 mM MgCl$_2$), 2 $\mu$l of 0.1M DTT, 10 mM dNTP (nucleotide triphosphates) mix and 1 $\mu$l of DEPC treated water. The reaction was incubated at 42° C. for 5 minutes. Finally, 5 $\mu$l of Superscript RT II was added and incubated at 42° C. for 2 more hours. The reaction was terminated on ice.

Second Strand Synthesis

The first strand product was adjusted to 93 $\mu$l with water and the following reagents were added on ice: 30 $\mu$l of 5×2nd strand buffer (100 mM TRIS-HCl (pH6.9),450 mM KCl, 23 mM MgCl$_2$, 0.75 mM $\beta$-NAD+, 50 mM (NH$_4$)$_2$SO$_4$), 3 $\mu$l of 10 mM dNTP (nucleotide triphosphates), 1 $\mu$l E. coli DNA ligase (10 units ) 1 $\mu$l RNase H (2 units), 4 $\mu$l DNA pol I (10 units). The reaction was incubated at 16° C. for 2 hours. The DNA from second strand synthesis was treated with T4 DNA polymerase and placed at 16° C. to blunt the DNA ends. The double stranded cDNA was extracted with 150 $\mu$l of a mixture of phenol and chloroform (1:1, v:v) and precipitated with 0.5 volumes of 7.5 M NH4OAc and 2 volumes of absolute ethanol. The pellet was washed with 70% ethanol and dried down at 37° C. to remove the residual ethanol. The double stranded DNA pellet was resuspended in 25 $\mu$l of water and the following reagents were added; 10 $\mu$l of 5×T4 DNA ligase buffer, 10 $\mu$l of Sal 1 adapters and 5 $\mu$l of T4 DNA ligase.

The ingredients were mixed gently and ligated overnight at 16° C. The ligation mix was extracted with phenol:chloroform:isoamyl alcohol, vortexed thoroughly and centrifuged at room temperature for 5 minutes at 14,000×g to separate the phases. The aqueous phase was transferred to a new tube and the volume adjusted to 100 ml with water. The purified DNA was size selected on a chromaspin 1000 column (Clontech) to eliminate the smaller cDNA molecules. The double stranded DNA was digested with Not1 restriction enzyme for 3–4 hours at 37° C. The restriction digest was electrophoresed on a 0.8% low melt agarose gel. The cDNA in the range of 1–5 kb was cut out and purified using Gelzyme (Invitrogen). The product was extracted with phenol:chloroform and precipitated with NH$_4$OAc and absolute ethanol. The pellet was washed with 70% ethanol and resuspended in 10 ml of water.

Ligation of cDNA to the Vector

The cDNA was split up into 5 tubes (2 $\mu$l each) and the ligation reactions were set up by adding 4.5 $\mu$l of water, 2 $\mu$l of 5×ligation buffer, 1 $\mu$l of p-Sport vector DNA (cut with Sal-1/Not1 and phosphatase treated) and 0.5 $\mu$l of T4 DNA ligase. The ligation was incubated at 40° C. overnight.

Introduction of Ligated cDNA into E.coli by Electroporation

The ligation reaction volume was adjusted to a total volume of 20 $\mu$l with water. Five milliliters of yeast tRNA, 12.5 ml of 7.5M NH$_4$OAc and 70 ml of absolute ethanol (−20° C.) was added. The mixture was vortexed thoroughly, and immediately centrifuged at room temperature for 20 minutes at 14000×g. The pellets were washed in 70% ethanol and each pellet was resuspended in 5 ml of water. All 5 ligations (25 ml) were pooled and 100 $\mu$l of DH10B electro-competent cells (Life Technologies) were electroporated with 1 ml of DNA (total of 20 electroporations), then plated out on ampicillin plates to determine the number of recombinants (cfu) per microliter. The entire library was seeded into 2 liters of Super Broth and maxipreps were made using Promega Maxi Prep kit and purified on cesium chloride gradients.

EXAMPLE 2

Library Screening/human Thalamus Library

One microliter aliquots of the human thalamus library were electroporated into Electromax DH10B cells (Life Technologies). The volume was adjusted to 1 ml with SOC media and incubated for 45 minutes at 37° C. with shaking. The library was then plated out on 150 cm$^2$ plates containing LB to a density of 10,000 colonies per plate. These cultures were grown overnight at 37° C.

A human BNaC4 probe was generated by a restriction digest of Incyte clone #4532692 that generated an internal fragment of about 400 base pairs in length. (Xho1/BamH1). The resulting 400 bp fragment was run on 1% agarose gel and purified using a QUIAquick Gel extraction kit (Quiagen). About 100 ng of the purified probe was labeled with alpha 32P using oligolabeling kit from Pharmacia and the labeled DNA was purified with S-200 columns (Pharmacia).

The library colonies were lifted on Protran nitrocellulose filters (Scheicher & Schuel) and the DNA was denatured in 1.5 M NaCl, 0.5 M NaOH. The filter disks were neutralized with 1.5 M NaCl, 1.0 M Tris-HCl, pH 7.5 and then UV cross-linked to the membrane using a UV-Stratalinker (Stratagene). The filters were washed several times in wash solution (1 M Tris-HCl, pH 8.0; 5 M NaCl; 0.5 M EDTA; 20% SDS) at 42° C. Then the disks were incubated in 1×southern pre-hybridization buffer (5'-3' Inc) containing 50% formamide and 100 ug/ml of sheared salmon sperm DNA (5'-3' Inc) for 6 hours at 42 C. Finally, hybridization was performed overnight at 42 C. in 1×hybridization buffer (5'-3') containing 50% formamide, 100 ng of sheared salmon sperm DNA in the presence of labeled probe ($5 \times 10^5$ to $1 \times 10^6$ cmp/ml of hybridization buffer).

The disks were washed twice in 233 SSC, 0.2% SDS at room temperature (20 min each) and once in 0.2×SSC, 0.1% SDS at 50 C. for 30 minutes. The membranes were than placed on sheets of filter paper, wrapped in Saran Wrap and exposed to the film at −20 C. overnight.

Positive clones were identified and collected by coring the colonies from the original plate. The colonies were incubated in LB for 1 hour at 37° C. Dilutions of the cultures were plated onto LB agar plates and the filter-lifting, hybridizing, washing, colony-picking procedure was repeated. Individual clones from the second screen were picked and digested with SalI/NotI to determine the size of the inserts, and the inserts were sequenced.

The full length clone was generated by PCR with Pfu polymerase using 10 ng of the sequenced library clone as a template and full length oligos with EcoR1 (FL 5'oligo SEQ.ID.NO.1) and NotI (FL 3' oligo SEQ.ID.NO.2) sites. FL 5' oligo (SEQ.ID.NO.1):
5' AACGTTGAATTCGCCACCATGCCGATC-GAGATTGTGTGCAAAATCAAATT 3'
FL3' oligo: (SEQ.ID.NO.2):
5' AACGTTGCGGCCGCAGCACCGTCCTAG-CAAGCAAAATCTTC 3'

The PCR product was digested with EcoR1 and NotI enzymes and cloned into pZeo/pSV2 expression vector (Invitrogen) and also into pGem HE. Large-scale preparation of DNA was done using a MEGA prep kit (Quiagen).

EXAMPLE 3

Cloning Human BNaC4 cDNA into a Mammalian Expression Vector

The human BNaC4 cDNA was cloned into the mammalian expression vector pCI Neo. The cloned PCR product was purified on a column (Wizard PCR DNA purification kit from Promega) and digested with NotI and EcoRI (NEB) to create cohesive ends. The product was purified by a low melting agarose gel electrophoresis. The pCI Neo vector was digested with Not1 and EcoR1 enzymes and subsequently purified on a low melt agarose gel. The linear vector was used to ligate to the human BNaC4 cDNA inserts. Recombinants were isolated, designated human BNaC4, and used to transfect mammalian cells (HEK293, COS-7 or CHO-K1 cells) using the Effectene non-liposomal lipid based transfection kit (Quiagen). Stable cell clones were selected by growth in the presence of zeocin. Single zeocin resistant clones were isolated and shown to contain the intact human BNaC4 gene. Clones containing the human BNaC4 cDNAs were analyzed for hBNaC4 protein expression. Recombinant plasmids containing human BNaC4 encoding DNA were used to transform the mammalian COS or CHO cells or HEK293 cells.

Cells expressing human BNaC4, stably or transiently, were used to test for expression of human BNaC4 using electrophysiological and viability assays. These cells are used to identify and examine other compounds for their ability to modulate, inhibit or activate the human BNaC4.

Cassettes containing the human BNaC4 cDNA in the positive orientation with respect to the promoter are ligated into appropriate restriction sites 3' of the promoter and identified by restriction site mapping and/or sequencing. These cDNA expression vectors are introduced into fibroblastic host cells for example COS-7 (ATCC# CRL1651), and CV-1 tat [Sackevitz et al., Science 238: 1575 (1987)], 293, L (ATCC# CRL6362)] by standard methods including but not limited to electroporation, or chemical procedures (cationic liposomes, DEAE dextran, calcium phosphate). Transfected cells and cell culture supernatants are harvested and analyzed for human BNaC4 expression as described herein.

All of the vectors used for mammalian transient expression can be used to establish stable cell lines expressing human BNaC4. Unaltered human BNaC4 cDNA constructs cloned into expression vectors are expected to program host cells to make human BNaC4 protein. The transfection host cells include, but are not limited to, CV-1-P [Sackevitz et al., Science 238: 1575 (1987)], tk-L [Wigler, et al. Cell 11: 223 (1977)], NS/0, and dHFr-CHO [Kaufman and Sharp, J. Mol. Biol. 159: 601, (1982)].

Co-transfection of any vector containing human BNaC4 cDNA with a drug selection plasmid including, but not limited to G418, aminoglycoside phosphotransferase; hygromycin, hygromycin-B phospholransferase; APRT, xanthine-guanine phosphoribosyl-transferase, will allow for the selection of stably transfected clones. Levels of human BNaC4 are quantitated by the assays described herein.

Human BNaC4 cDNA constructs are also ligated into vectors containing amplifiable drug-resistance markers for the production of mammalian cell clones synthesizing the highest possible levels of human BNaC4. Following introduction of these constructs into cells, clones containing the plasmid are selected with the appropriate agent, and isolation of an over-expressing clone with a high copy number of plasmids is accomplished by selection in increasing doses of the agent.

The expression of recombinant human BNaC4 is achieved by transfection of full-length human BNaC4 cDNA into a mammalian host cell.

EXAMPLE 4

Distribution of Human BNaC4 in cDNA Libraries

The tissue distribution of BNaC4 mRNAs was determined by semi-quantitative PCR. A primer set specific to BNaC4 (GCTTCCAGACCTTTGTGTCC [SEQ.ID.NO.3]; CAGAATGGTCTCATTGCCTGG [SEQ.ID.NO.4]) was used to complete amplification of a portion of the BNaC4 mRNA via PCR using cDNAs from constructed libraries (see Example 1). To gain increased specificity and sensitivity, an oligonucleotide (GAGCTCAGGG AGCCTGAGCTTCAGGGCTACTCGGCCTACA [SEQ.ID.NO.5]) was phosphorylated using $\gamma$-$^{32}$P-ATP with polynucleotide kinase as described by manufacturer (Amersham Pharmacia Biotech, Piscataway, N.J.) and annealed to denatured PCR products and resolved by 6% polyacrylamide gel electrophoresis. The subsequent gel was then dried down and imaged (PhosphorImager 445SI, Molecular Dynamics).

Figure 8:
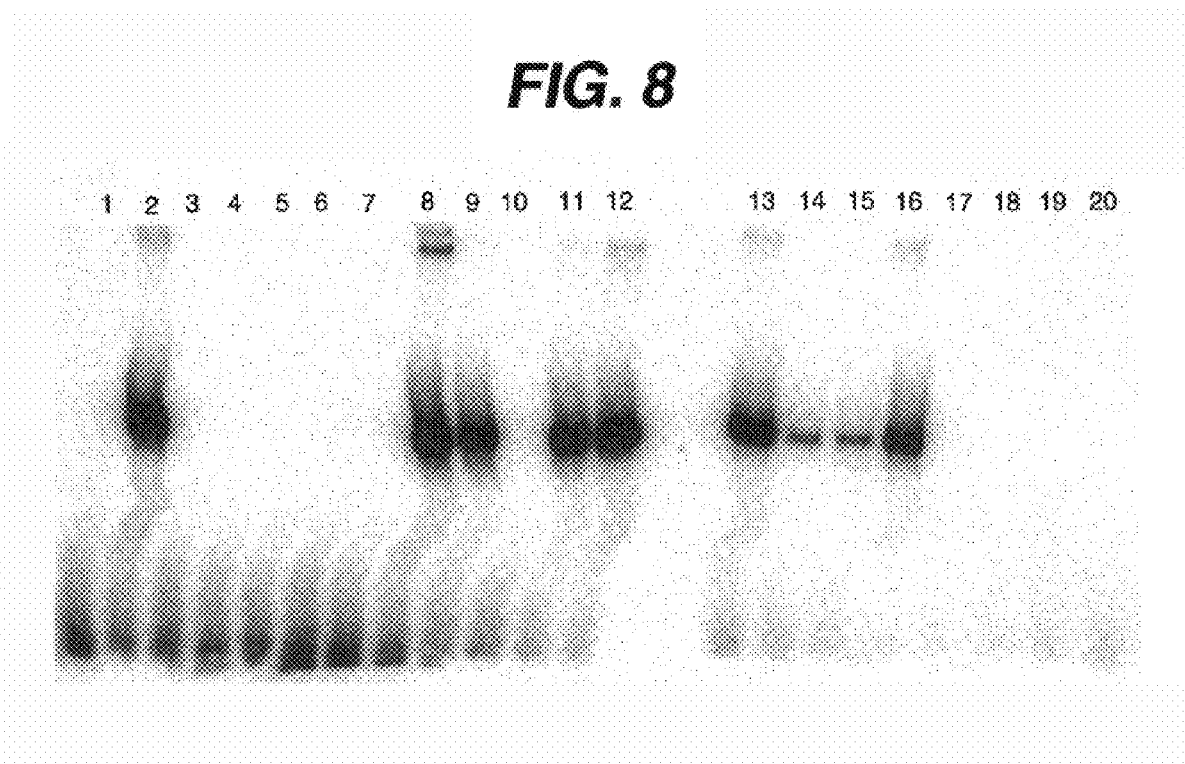
FIG. 8—Expression of human BNaC4 in cDNA libraries. The PCR-based tissue distribution of the human BNaC4 is shown. Lanes are labeled as indicated: Lane 1: spleen; lane 2: thalamus; lane 3: placenta; lane 4: heart; lane 5: liver; lane 6: lung; lane 7 uterus; lane 8: pituitary; lane 9: spinal cord; lane 10: bone marrow; lane 11: hippocampus; lane 12: hypothalamus; lane 13: small intestine; lane 14: dorsal root ganglia; lane 15: cerebellum; lane 16: cortex; lane 17–20: negative controls.

As shown in FIG. 8, PCR-based tissue distribution analysis reveals that the BNaC4 mRNA is expressed in cDNA libraries constructed from human cerebral cortex, thalamus, pituitary, spinal cord, hippocampus, hypothalamus, small intestine, DRG and cerebellum. No detectable cDNA was observed in spleen, placenta, heart, liver, lung, uterus and bone marrow.

There is overlap of the tissue distribution based on the presence of the hBNaC4 cDNA in cDNA libraries with ASIC1, ASIC2 and ASIC3 (see highlighted tissues in TABLE 2), suggesting heteromers may exist which have altered pH dependence and/or kinetics.

EXAMPLE 5

Characterization of Functional Protein Encoded by Human BNaC4 in Xenopus Oocytes

*Xenopus laevis* oocytes were prepared and injected using standard methods previously described and known in the art (Fraser et al., 1993). Ovarian lobes from adult female *Xenopus laevis* (Nasco, Fort Atkinson, Wis.) were teased apart, rinsed several times in nominally Ca-free saline containing: 82.5 mM NaCl, 2.5 mM KCl, 1 mM MgCl$_2$, 5 mM HEPES, adjusted to pH 7.0 with NaOH (OR-2), and gently shaken in OR-2 containing 0.2% collagenase Type 1 (ICN Biomedicals, Aurora, Ohio) for 2–5 hours. When approximately 50% of the follicular layers were removed, Stage V and VI oocytes were selected and rinsed in media consisting of 75% OR-2 and 25% ND-96. The ND-96 contained: 100 mM NaCl, 2 mM KCl, 1 mM MgCl$_2$, 1.8 mM CaCl$_2$, 5 mM HEPES, 2.5 mM Na pyruvate, gentamicin (50 ug/ml), adjusted to pH 7.0 with NaOH. The extracellular Ca$^{+2}$ was gradually increased and the cells were maintained in ND-96 for 2–24 hours before injection. For in vitro transcription, pGEM HE (Liman et al., 1992) containing human BNAC4 was linearized with NheI and transcribed with T7 RNA polymerase (Promega) in the presence of the cap analog m7G(5')ppp(5')G. The synthesized cRNA was precipitated with ammonium acetate and isopropanol, and resuspended in 50 $\mu$l nuclease-free water. cRNA was quantified using formaldehyde gels (1% agarose, 1×MOPS , 3% formaldehyde) against 1,2 and 5 $\mu$l RNA markers (Gibco BRL, 0.24–9.5 Kb).

Oocytes were injected with 50 nl of the human BNaC4 RNA (0.002–5 ng). Control oocytes were injected with 50 nl of water. Oocytes were incubated for 1–6 days in ND-96 before analysis for expression of the human BNaC4. Incubations and collagenase digestion were carried out at room temperature. Injected oocytes were maintained in 48 well cell culture clusters (Costar; Cambridge, Mass.) at 18° C. Whole cell agonist (protons)-induced currents were measured 1–6 days after injection with a conventional two-electrode voltage clamp (GeneClamp500, Axon Instruments, Foster City, Calif.) using standard methods previously described and known in the art (Dascal, Nathan (1987) The use of Xenopus oocytes for the study of ion channels. CRC Critical reviews in Biochemistry 22:317–387). The microelectrodes were filled with 3 M KCl, which had resistances of 1 and 2 M$\Omega$. Cells were continuously perfused with ND96 at ~10 ml/min at room temperature unless indicated. Membrane voltage was clamped at –70 mV unless indicated.

Oocytes injected with human BNaC4 had properties that were different from controls in 2 respects. First, injection of BNaC4 cRNA caused a dramatic decrease in oocyte viability compared to water-injected sister control oocytes 1–4 days after injection (FIG. 4). Second, BNaC4 injection produced a low pH activated conductance (FIG. 5). Furthermore, there was a tendency for the cells injected with BNaC4 (2 ng cRNA per oocyte) to require a larger current to hold the membrane potential at –70 mV (–1.2+/–0.4 uA (n=12) vs. –0.27+/–0.05 uA (n=10) (p<0.05) in Ca2+ ND-96 and –5.92+/–0.96 uA (n=5) vs. –0.41+/–0.10 uA (n=3) in Ba2+-ND96 (p<0.005). The holding current was not significantly different comparing oocytes injected with 0.02 ng cRNA and water-injected oocytes.

Viability

Functional expression of human BNaC4 in Xenopus oocytes is shown: viability of oocytes maintained in ND-96 containing 2 Ca$^{2+}$ was significantly diminished 1–4 days after injection with BNaC4 (1–5 ng) CRNA (FIG. 4). Data for BNaC4 and control water-injected oocytes were similar in 6 separate experiments and combined. Dead oocytes were determined visually using a Bauch and Lomb dissecting microscope at 30×magnification. The percentage of viable oocytes injected with BNaC4 were significantly lower than water injected control oocytes: only about 13% of oocytes injected with BNaC4 (n=274) survived to 1–4 days after injection compared to 89% of sister vehicle-injected control oocytes (n=162) maintained under essentially identical conditions. Data were analyzed using Chi square analysis and the difference was found to be highly significant (p=1.7×e-45) (FIG. 4). The effect of hBNaC4 cRNA on oocyte viability was dose dependent since injection of 0.02 ng was similar to control values.

Responsiveness of Human BNaC4-injected Oocytes to Low pH Salines

Figure 5B:
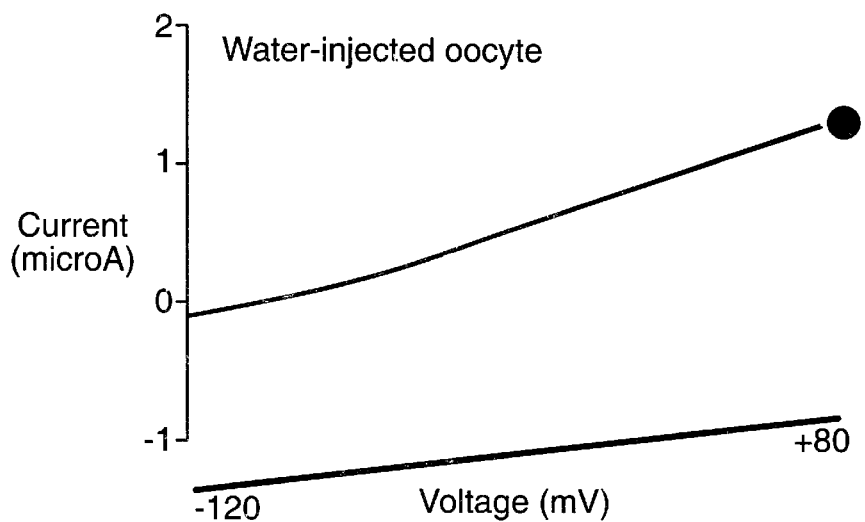

Functional expression of human BNaC4 in Xenopus oocytes is shown: activation by pH 5.5. FIG. 5A shows the whole cell current activated by bath application of extracellular saline at pH 5.5 (black circle). The oocyte was recorded 3 days after injection of 2 ng hBNaC CRNA. The current-voltage relationship was obtained by applying a voltage ramp from –120 to +80 mV at a rate of 0.5 mV/msec every 2 sec. Similar results were obtained from 4 sets of injected oocytes. Oocytes were constantly perfused with Ca2+ ND-96 pH 8.3. In FIG. 5B, application of low pH to a water-injected oocyte from the same experiment had no effect other than a slight reversible decrease in conductance. When the data from 4 separate experiments were combined, there was a significant difference in the responsiveness to pH 5.5 saline in hBNaC4 injected vs. water injected controls. The increase in current measured at +80 mV was 498+/–194 nA (mean+/–SEM; n=7) vs. 14+/–10 nA (n=10) for oocytes injected with 2–5 ng hBNaC cRNA vs. water, respectively (p<0.05). The BNaC4 oocytes tested produced currents of at least +60 nA (measured at +80 mV at the end of a voltage ramp protocol) (range +60 to +1240 nA). Half of the water-injected oocytes revealed no fast increase in conductance. The pH5.5-induced fast increase in conductance was blocked by 40+/–13% (n=3) by bath application of 200 uM amiloride. Detailed analyses of the kinetics of the response were not possible since a secondary effect (usually a slowly activating decrease in conductance) precluded the isolation of the initial response. The reversal potential of the initial response was 6+/−5 mV (n=7). Under similar experimental conditions, the Vrev for ligand-gated non-selective cation channels is about −15 mV (Dubin, A. E. (1999) JBC 274: 30799–30810), suggesting Na+ may be the more permeant cation through hBNaC homomers expressed in oocytes.

EXAMPLE 6

Characterization of Human BNaC4 in Mammalian Cell Lines

Human HEK293 cells were transfected with human BNaC4 (phBNaC4) together with the pEGFP vector (Clontech). Transient transfections 2 μg of phBNAC4 together with 1 μg pEGFP per $10^6$ cells per 100 mm dish are performed using the Effectene transfection kit (Quiagen; 301425). Two to three days after transfection, cells are plated onto 12 mm round coverslips and maintained in growth media overnight. After one day, wells were tested for their whole cell response to application of low pH from nearby puffer pipettes using whole cell voltage clamp. Cells expressing GFP were tested (GFP-positive cells). Transfections with vector alone with GFP were used as controls (GFP-positive).

Stable cell lines expressing human BNaC4 are constructed. After three days the cells are selected in the presence of neomycin (500 μg/ml) and grown through three 1:10 dilution passages for approximately two weeks. Individual colonies are picked and grown in 6-well dishes. Cells expressing human BNaC4 are tested for their response to low pH using electrophysiological voltage clamp techniques and cell viability assays and compared to responses obtained from sister cells stably expressing only the cloning vector (pCINeo).

The whole cell patch clamp technique (Hamill et al., 1981 Pfluegers Arch. 391:85–100) was used to record proton-induced currents from HEK293 transiently expressing human BNaC4 maintained for >2 days on 12 mm coverslips. Cells were visualized using a Nikon Diaphot 300 with DIC Nomarski optics. Cells were continuously perfused in a physiological saline (~0.5 ml/min) at pH 7.5 or 8.2 as indicated. The standard physiological saline ("Tyrodes") contained: 130 mM NaCl, 4 mM KCl, 1 mM $CaCl_2$, 1.2 mM $MgCl_2$, and 10 mM hemi-Na-HEPES (pH 7.3, 295–300 mOsm as measured using a Wescor 5500 vapor-pressure (Wescor, Inc., Logan, Utah). Recording electrodes were fabricated from borosilicate capillary tubing (R6; Garner Glass, Claremont, Calif.), the tips are coated with dental periphery wax (Miles Laboratories, South Bend, Ind.), and have resistances of 1–2 MΩ when containing intracellular saline: 100 mM K-gluconate, 25 mM KCl, 0.483 mM $CaCl_2$, 3 mM $MgCl_2$, 10 mM hemi-Na-HEPES and 1 mM $K_4$-BAPTA (100 nM free $Ca^{+2}$); pH 7.4, with dextrose added to achieve 290 mOsm). Liquid junction potentials were −18 mV using standard pipette and bath solutions as determined both empirically and using the computer program JPCalc (Barry, P. H. (1994) J. Neurosci. Methods 51:107–116). All voltages shown were corrected for liquid junction potential. Current and voltage signals were detected and filtered at 2 kHz with an Axopatch ID patch-clamp amplifier (Axon Instruments, Foster City, Calif.), digitally recorded with a DigiData 1200B laboratory interface (Axon Instruments), and PC compatible computer system and stored on magnetic disk for off-line analysis. Data acquisition and analysis were performed with PClamp software.

Apparent reversal potentials ($V_{rev}$) of ligand-induced conductance changes were determined using a voltage-ramp protocol (Dubin, A. E. et al., (1999) J. Neurosci. 19: 1371–1381). Voltage ramps were applied every 2 seconds and the resulting whole cell ramp-induced currents were recorded. Usually the voltage was ramped from negative to positive to negative values. The current required to clamp the cells at −88 mV was continuously monitored. Low pH-induced conductances were determined from whole-cell currents elicited by a voltage-ramp protocol in the presence and absence of protons. Voltage ramp-induced currents measured before (control) and in the presence of low pH were compared to reveal the effect of low pH on the channel to modulate the channel current output. The voltage at which there was no net ligand-induced current was determined ($V_{rev}$). The total membrane capacitance ($C_m$) was determined as the difference between the maximum current after a 30 mV hyperpolarizing voltage ramp from −68 mV generated at a rate of 10 mV/ms and the steady state current at the final potential (−98 mV) (Dubin, A. E. et al., (1999) J. Neurosci. 19: 1371–1381).

Epi-fluorescence attachments for the Nikon Diaphot300 included a HMX-4 Lamphouse, C-FC EPI-FL collector lens, 100 W Mercury lamp and power supply HBO-100W, and filter cubes EF-4 B-2E/C and EF 4-G2E. A vector expressing the green fluorescent protein (GFP; pEGFP vector, Clontech) was co-transfected with hBNaC4 at a 1:2 ratio. GFP-positive cells are likely to also be transfected with BNaC4 when transfected at a 1:2 ratio, and formed the basis of determining transfection efficiency and selection of cells to assay for BNaC4 activity.

Transient transfection of HEK293 cells with hBNaC4 revealed 2 dramatic differences compared to control vector only-transfected cells. First, there was a decrease in GFP-positive cell viability in cells transfected with hBNaC4. Second, application of low pH solutions from nearby puffer pipettes rapidly increased a conductance in hBNaC4-transfected cells consistent with being mediated in part by Na+. This effect was not observed in GFP-positive cells co-transfected with vector only.

hBNaC4 Decreased Cell Viability

Cells most likely to be transfected by hBNaC4 or vector were identified by the presence of green fluorescent protein. While not all cells expressing GFP will be transfected with the second vector, it is likely that vector-transfected cells will express GFP. The viability of GFP-positive cells transiently transfected with hBNaC4 was significantly diminished after 3–6 days. Data were obtained from 2 separate experiments. Cells were transfected with vectors expressing human BNaC4 or GFP and maintained in growth medium without selection for 3–4 days, 5 or 6 days before visualizing on a Nikon Diaphot 300 with Nomarski optics equipped with epi-fluorescence to visualize green fluorescence protein.

Figure 6B:
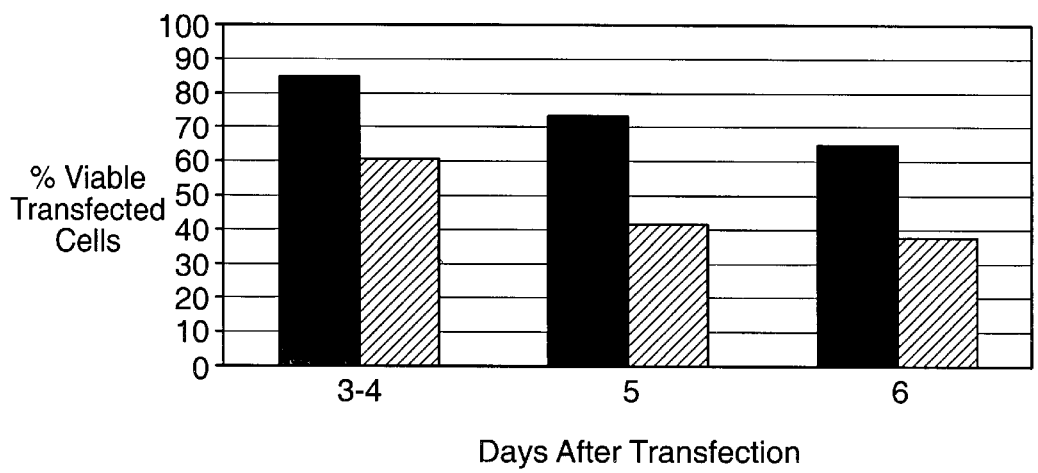
FIG. 6—Functional expression of human BNaC4 in HEK293 cells is shown: viability of GFP-positive cells transiently transfected with hBNaC4 and GFP was significantly diminished after 3–6 days. Data were obtained from 2 separate experiments. Cells were transfected with human BNaC4 and GFP vectors and maintained in growth medium without selection for 3–4 days, 5 or 6 days before visualizing on a Nikon Diaphot 300 with Nomarski optics with epifluorescence to visualize the presence of green fluorescence protein. Dead cells were determined visually (see Example 7). a. GFP-positive cells were examined on 3–6 coverslips from 2 separate transfections. The data are grouped into 3–4, 5 or 6 days after transfection. Data were analyzed using Chi square analysis. b. Graphical representation of the percentage of viable GFP-positive cells in vector-transfected (black bar) and hBNaC4 transfected (hatched bar) cells given in the bottom row of each time point shown in (a). Transfection of hBNaC4 produced a significant reduction in the percentage of viable cells compared to control. The initial transfection efficiency for human BNaC4 and vector control was 30 and 15–20%, respectively.

HEK293 cells transfected with phBNaC4 appeared to loose extensions and attachments to the substrate, acquire vacuoles and blebs, and die, a mode of cell death reported for MDEG gain of function mutants (Waldmann et al., 1996) and the degenerin-induced neurodegeneration in C. elegans (Chalfie and Wolinsky, 1990; Driscoll and Chalfie, 1991; Garcia-Anoveros et al., 1998; Hall et al., 1997). In FIG. 6a, GFP-positive cells were examined from 3–6 coverslips from 2 separate transfections and dead cells were determined visually. The data are grouped into 3–4, 5 or 6 days after transfection. Data were analyzed using Chi square analysis. The initial transfection efficiency of GFP vector transfection in the presence of the BnaC4 vector (phBNaC4) (30%) was similar to the efficiency in the presence of the pCIneo vector only (15–20%). At all days investigated, there were significantly fewer surviving GFP-positive cells when they were co-transfected with phBNaC4 compared to controls transfected with pCIneo. This difference is graphically presented in (FIG. 6b), where the percent viable GFP-positive cells transfected with pCIneo (black bar) and phBNaC4 (hatched bar) are shown.

Activation of a Membrane Conductance by Low pH was Dependent on hBNaC4

Figure 7A:
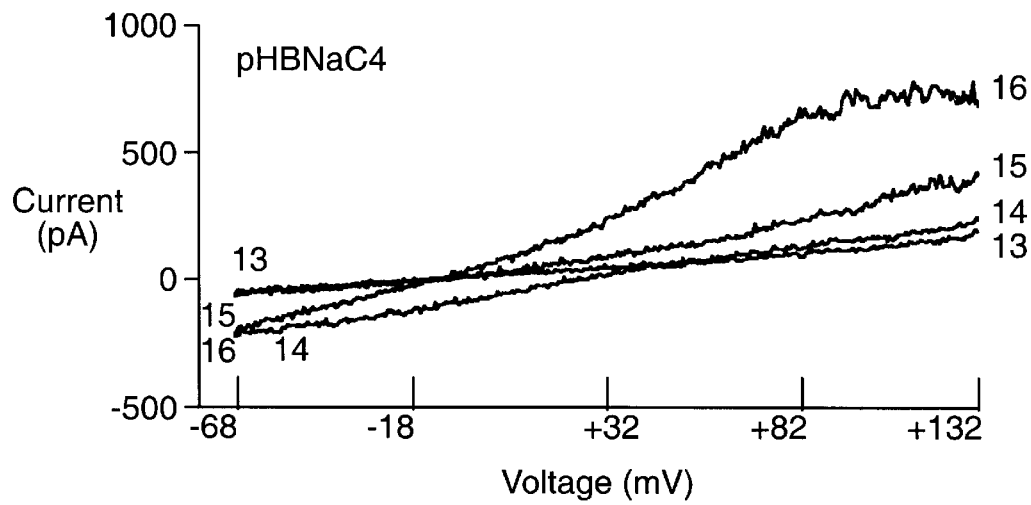
FIG. 7—Function in mammalian HEK293 cells transiently expressing human BNaC4: pH 4.5 produced an increase in conductance that appeared to be biphasic in phBNaC4-transfected cells (a). An initial rapid increase in whole cell current had a reversal potential of +54 mV under ionic conditions in which $E_{Na}$ was predicted to be +84 mV. A secondary increase in current was observed which reversed near 0 mV (−14 mV in this example). The voltages shown are corrected for a junction potential of −18 mV. Whole cell voltage-ramp induced currents were measured every 2.5 sec. The numbers next to each trace refer to the sweep number. There was partial recovery and then the cell membrane became very leaky. Vector controls showed no response similar to that shown here for hBNaC4-transfected cells. b. pH4.5 applied to a GFP-positive cell transfected with pEGFP +pCINeo vector control produced no increase in conductance.
Figure 7B:
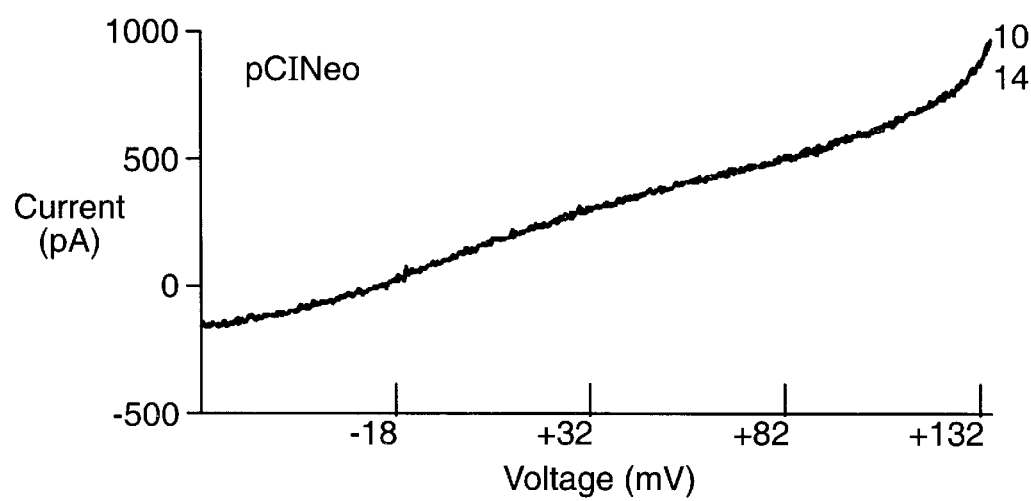

The whole cell configuration of the patch clamp technique was achieved by rupturing the patch of membrane under the pipette. Cells were held at −68 mV and challenged with hyperpolarizing voltage ramps to obtain current voltage relationships before, during and after application of low pH salines from nearby puffer pipettes. In BNaC4-transfected but not vector-only controls, low pH evoked a rapidly activating increase in conductance in 15 of 18 cells. Currents were measured at −68 and +82 mV on voltage ramp induced current traces and the difference between the activated and the initial control currents was determined at these voltages. The entire current-voltage curve is shown in FIG. 7. The threshold for the increase was about pH 4.75. The currents elicited by pH 4.5 at −50 and +100 mV in the first 2–3 seconds after challenge were variable from cell to cell [range: −35 to −4500 pA at −50 mV and 20 to 2015 pA at +100 mV] and averaged −753+/−297 pA (n=16) and 453+/−248 pA (n=9), respectively. The conductance increased rapidly upon exposure to pH 4.5 and was consistent with a largely Na+-mediated current. The current-voltage relationship subsequently appeared to shift to more negative potentials, consistent with low pH producing a secondary component mediated by non-selective cations. Some members of the ASIC family of channels are permeable to Ca2+ (eg., ASIC IA (Waldmann et al., 1997)), and it is possible that the secondary effect is activated by Ca2+.

The cells transfected with hBNaC4 and responding to low pH were more susceptible to cell death shortly after activation of large currents than control cells transfected with vector and GFP. Reversibility of the pH induced effect was most easily observed using a stimulus of pH 4.75 which produced about 5% of the response to pH 4.5 (−40+/−17 pA (n=3) and +20+/−10 pA (n=3) at −50 and +100 mV respectively).

The reversal potential for the low pH activated current was +42+/−10 mV (n=15). This value takes into account the junction potential due to the use of intracellular and extracellular salines with different Cl-concentrations. The reversal potential could be determined using voltage ramp protocols at a ramp speed of 1 mV/ms (200 msec total time required). Under the recording conditions used in these experiments, the predicted reversal potential for a Na-selective current would be +82 mV. Thus, the data are consistent with human BNaC4 forming homomers that are highly but not completely Na-selective.

We investigated the effect of amiloride on the current elicited by pH 4.5. Amiloride is a known inhibitor of current through the ASIC family of channels with a wide range of potency (see Background of invention). Cells were challenged with pH4.5 in the presence of 500 uM amiloride. The same cells were subsequently tested for their response to pH 4.5 alone. Amiloride blocked the pH effect by 98+/−2% (n=3).

The threshold for activation appeared to be near pH 4.75, similar to that observed for MDEG1 (Bassilana et al., 1997).

EXAMPLE 7

Primary Structure of the Human BNaC4 Protein

The present invention describes human BNaC4. The nucleotide sequence of human BNaC4 cDNA revealed single large open reading frame of about 1620 base pairs encoding 539 amino acids. The cDNA for BNAC4 has 5' and 3'-untranslated extensions of about 164 and about 744 nucleotides, respectively. The first in-frame methionine was designated as the initiation codon for an open reading frame that predicts human BNAC4 protein with an estimated molecular mass ($M_r$) of about 59,203 Da. The present invention appears to be the human homolog of the rat SPASIC (Akopian, England, Chen and Wood (unpublished); Genbank AJ242554). At the amino acid level human BNaC4 is 97% identical and 98.5% similar to the rat SPASIC. At the nucleotide level in the coding region, human and rat sequences are about 91% identical. A human genetic sequence AC009955 (human clone NH0256123) contains part of the human BNaC4 gene.

| Nuc # incl 5'UT | AC009955 unordered pieces (2 contigs: 30239–32330 and 66109–70108) |
|---|---|
| 582–727 | 32299–32157 |
| 728–855 | 32059–31935 |
| 855–1019 | 31751–31592 |
| 1019–1183 | 31751–31592 |
| 1193–1239 | 31188–31142 |
| 1400–1506 | 66350–66456 |
| 1504–1620 | 66645–66759 |

There are occasional single base deletions in the genomic sequence compared to the cDNA described in the present invention.

The Homo sapiens clone 15_J_2 appears to encode the 5'UT 162 nucleotides of the present invention.

The predicted human BNaC4 proteins were aligned with nucleotide and protein databases and found to be related to members of the ASIC family. There are several conserved motifs found in this family of receptor including 2 predicted transmembrane regions (hydrophobic regions of 20 amino acids) and large putative extracellular segment between the 2 transmembrane segments (about 354 amino acids). According to the current topological model based on primary structure analysis and biochemical experiments, a large domain of 354 amino acids faces the extracellular side of the plasma membrane (Canessa et al., 1994; Canessa et al., 1994).

The percent identity of hBNaC4 with the other members of the ASIC family is overall about 48%. The percent identity of BNaC3 with BNaC1 and BNaC2 is 47% abd 48%, respectively. Thus the human BNaC4 described herein is clearly a separate branch of the ASIC gene family.

Percent identity at amino acid level (using LFASTA; Pearson and Lipman 1988 PNAS 85:2444–2448):

| | hASIC1 = hBNaC2 | hASIC2 = hBNaCl**, MDEG, MDEG1 | hASIC3 = hBNaC3 = DRASIC |
|---|---|---|---|
| hBNaC4 entire cds | 44.5* | 47.5 | 47.9 | hASIC1 = U50352; ((Price et al., 1996));
hASIC2 = U78181 ((Garcia Anoveros et al., 1997));
hASIC3 = AF057711 (Sequela was first in Genbank by one week; (Seguela and Babinski, 1999); other human DRASIC sequences are AF095897 (de Weille et al., 1998) and AB010575 (Ishibashi, K., unpublished).
*rat ASIC (U94403) is 47.8% identical.
**hBNaC2 has two alternatively spliced isoforms U78180 and U78181.

The N- and C-terminal regions are most divergent among human ASIC1, ASIC2 and ASIC3. The most conserved sequences between these family members are in the putative extracellular domain: FPAVTLCNxNxxR, GKCY, GLxIMLDIQQxEYLP, FExGxxVQIHSQxEPPxIxxLGxGVxPGxQTFVxxQ, CRMVxMPG as well as the MII domain. The extracellular loop is highly cysteine-rich, as are other members of this superfamily. Three are 15 cys residues in the putative extracellular loop of human BNaC4 including C281, the cysteine residue that is not conserved in hASIC2.

The BNaC4 has two potential myristoylation sites: [GVSPGF] and [GGQMGLFIGA] in the putative extracellular domain between MI and MII. Two putative N-linked glycosylation sites at N191 and N376; the former is conserved in DRASIC, the latter is 27 amino acids upstream of the putative N-linked glycosylation site in DRASIC. Putative phosphorylation sites include: 1 potential PKC phosphorylation site (S394) that is in the putative extracellular domain; 4 potential casein kinase II phosphorylation sites: T245, S257, S280 and T457 [however, the first 3 are in the putative extracellular domain and the last is in the putative MII domain;2 potential mammary gland casein kinase phosphorylation sites (SxE): S246, S257; 1 potential tyrosine kinase phosphorylation site: Y310 [however, it is present in the putative extracellular domain]. The functional impact of phosphorylation of these domains may be important in the context of heterologous sensitization of cellular responses induced by metabotropic and growth factors. There are no putative CaM binding domains (IQ xx F/Y RIK G/K xx R/K R/K) in the present invention. There are no putative PKA phosphorylation sites.

There were 2 bases in the coding sequence that were consistently different in one of 10 independent cDNA library clones. These Keto and pyrimidine differences caused an L to become R and A to V in the C-terminal sequence: . . . S[L/R]GR[A/V] EGGGVSSLLPNHHHPHGPPGGLFEDFAC (See FIG. 3).

EXAMPLE 8

Cloning Human BNaC4 cDNA into *E. coli* Expression Vectors

Recombinant human BNaC4 is produced in *E. coli* following the transfer of the human BNaC4 expression cassette into *E. coli* expression vectors, including but not limited to, the pET series (Novagen). The pET vectors place human BNaC4 expression under control of the tightly regulated bacteriophage T7 promoter. Following transfer of this construct into an *E. coli* host that contain a chromosomal copy of the T7 RNA polymerase gene driven by the inducible lac promoter, expression of human BNaC4 is induced when an appropriate lac substrate (IPTG) is added to the culture. The levels of expressed human BNaC4 are determined by the assays described herein.

The cDNA encoding the entire open reading frame for human BNaC4 is inserted into the NdeI site of pET[16]11a. Constructs in the positive orientation are identified by sequence analysis and used to transform the expression host strain BL21. Transformants are then used to inoculate cultures for the production of human BNaC4 protein. Cultures may be grown in M9 or ZB media, whose formulation is known to those skilled in the art. After growth to an $OD_{600}=1.5$, expression of human BNaC4 is induced with 1 mM IPTG for 3 hours at 37° C.

EXAMPLE 9

Cloning Human BNaC4 cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculovirus expressing human BNaC4 cDNA is produced by the following standard methods (InVitrogen Maxbac Manual): the human BNaC4 cDNA constructs are ligated into the polyhedron gene in a variety of baculovirus transfer vectors, including the pAC360 and the BlueBac vector (InVitrogen). Recombinant baculovirus are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells and recombinant pBlueBac viruses are identified on the basis of β-galactosidase expression (Summers, M. D. and Smith, G. E., Texas Agriculture Exp. Station Bulletin No. 1555). Following plaque purification, human BNaC4 expression is measured by the assays described herein.

The cDNA encoding the entire open reading frame for human BNaC4 is inserted into the BamHI site of pBlueBacII. Constructs in the positive orientation are identified by sequence analysis and used to transfect Sf9 cells in the presence of linear AcNPV mild type DNA.

Authentic, active human BNaC4 is found in the cytoplasm of infected cells. Active human BNaC4 is extracted from infected cells by hypotonic or detergent lysis.

EXAMPLE 10

Cloning Human BNaC4 cDNA into a Yeast Expression Vector

Recombinant human BNaC4 is produced in the yeast *S. cerevisiae* following insertion of the optimal human BNaC4 cDNA cistron into expression vectors designed to direct the intracellular or extracellular expression of heterologous proteins. In the case of intracellular expression, vectors such as EmBLyex4 or the like are ligated to the human BNaC4 cistron [Rinas, U. et al., Biotechnology 8: 543–545 (1990); Horowitz B. et al., J. Biol. Chem. 265: 4189–4192 (1989)]. For extracellular expression, the human BNaC4 cistron is ligated into yeast expression vectors which fuse a secretion signal (a yeast or mammalian peptide) to the $NH_2$ terminus of the human BNAC4 protein [Jacobson, M. A., Gene 85: 511–516 (1989); Riett L. and Bellon N. Biochem. 28: 2941–2949 (1989)].

These vectors include, but are not limited to pAVE1>6, which fuses the human serum albumin signal to the expressed cDNA [Steep O. Biotechnology 8: 42–46 (1990)], and the vector pL8PL which fuses the human lysozyme signal to the expressed cDNA [Yamamoto, Y., Biochem. 28: 2728–2732)]. In addition, human BNAC4 is expressed in yeast as a fusion protein conjugated to ubiquitin utilizing the vector pVEP [Ecker, D. J., J. Biol. Chem. 264: 7715–7719 (1989), Sabin, E. A., Biotechnology 7: 705–709 (1989), McDonnell D. P., Mol. Cell Biol. 9: 5517–5523 (1989)]. The levels of expressed human BNaC4 are determined by the assays described herein.

EXAMPLE 11

Purification of Recombinant Human BNaC4

Recombinantly produced human BNaC4 may be purified by antibody affinity chromatography.

Human BNaC4 antibody affinity columns are made by adding the anti-human BNaC4 antibodies to Affigel-10 (Bio-Rad), a gel support that is pre-activated with N-hydroxysuccinimide esters such that the antibodies form covalent linkages with the agarose gel bead support. The antibodies are then coupled to the gel via amide bonds with the spacer arm. The remaining activated esters are then quenched with IM ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatant or cell extract containing solubilized human BNaC4 is slowly passed through the column. The column is then washed with phosphate-buffered saline together with detergents until the optical density (A280) falls to background, then the protein is eluted with 0.23 M glycine-HCl (pH 2.6) together with detergents. The purified human BNaC4 protein is then dialyzed against phosphate buffered saline.

REFERENCES

Babinski, K., Le, K.-T., and Seguela, P. (1999). Molecular cloning and regional distribution of a human proton receptor subunit with biphasic functional properties. J. Neurochem. 72, 51–57.

Bassilana, F., Champigny, G., Waldmann, R., de Weille, J. R., Heurteaux, C., and Lazdunski, M. (1997). The acid-sensitive ionic channel subunit ASIC and the mammalian degenerin MDEG form a heteromultimeric H+-gated Na+ channel with novel properties. J. Biol. Chem. 272, 28819–28822.

Benson, C. J., Eckert, S. P., and McCleskey, E. W. (1999). Acid-evoked currents in cardiac sensory neurons: a possible mediator of myocardial ischemic sensation. Circ. Res. 84, 921–928.

Bevan, S., and Yeats, J. (1991). Protons activate a cation conductance is a subpopulation of rat dorsal root ganglion neurones. J Physiol 433, 145–161.

Canessa, C. M. (1996). What is new about the structure of the epithelial Na+ channel? In News Physiol. Sci., pp. 195–201.

Canessa, C. M., Merillat, A.-M., and Rossier, B. C. (1994). Membrane topology of the epithelial sodium channel in intact cells. Am. J. Physiol. 267, C1682-C1690.

Canessa, C. M., Schild, L., Buell, G., Thorens, B., Gautschi, I., Horisberger, J. D., and Rossier, B. C. (1994). Amiloride-sensitive epithelial Na+ channel is made of three homologous subunits. Nature (London) 367, 463–7.

Chalfie, M., and Wolinsky, E. (1990). The identification and suppression of inherited neurodegeneration in Caenorhabditis elegans. Nature (London) 345, 410–16.

Chen, C.-C., England, S., Akopian, A. N., and Wood, J. N. (1998). A sensory neuron-specific, proton-gated ion channel. Proc. Natl. Acad. Sci. U. S. A. 95, 10240–10245.

Coscoy, S., De Weille, J. R., Lingueglia, E., and Lazdunski, M. (1999). The pre-transmembrane 1 domain of acid-sensing ion channels participates in the ion pore. J. Biol. Chem. 274, 10129–10132.

de Weille, J. R., Bassilana, F., Lazdunski, M., and Waldmann, R. (1998). Identification, functional expression and chromosomal localization of a sustained human proton-gated cation channel. FEBS Lett. 433, 257–260.

Driscoll, M., and Chalfie, M. (1991). The mec-4 gene is a member of a family of Caenorhabditis elegans genes that can mutate to induce neuronal degeneration. Nature (London) 349, 588–93.

Fraser, S. P., Moon, C., and Djamgoz, M. B. A. (1993). Electrophysiology of Xenopus oocytes: An expression system in molecular neurobiology., D. Wallis, ed. (Oxford, UK: IRL).

Fyfe, G. K., and Canessa, C. M. (1998). Subunit composition determines the single channel kinetics of the epithelial sodium channel. J. Gen. Physiol. 112, 423–432.

Garcia Anoveros, J., Derfler, B., Neville Golden, J., Hyman, B. T., and Corey, D. P. (1 997). BNaC1 and BNaC2 constitute a new family of human neuronal sodium channels related to degenerins and epithelial sodium channels. Proc. Natl. Acad. Sci. U. S. A. 94, 1459–1464.

Garcia-Anoveros, J., Garcia, J. A., Liu, J.-D., and Corey, D. P. (1998). The nematode degenerin UNC-105 forms ion channels that are activated by degeneration- or hypercontraction-causing mutations. Neuron 20, 1231–1241.

Garcia-Anoveros, J., Ma, C., and Chalfie, M. (1995). Regulation of Caenorhabditis elegans degenerin proteins by a putative extracellular domain. Curr. Biol. 5, 441–8.

Ghosh, A., and Greenberg, M. E. (1995). Calcium signaling in neurons: molecular mechanisms and cellular consequences. In Science (Washington, D. C.), pp. 239–47.

Giffard, R. G., Monyer, H., Christine, C. W., and Choi, D. W. (1990). Acidosis reduces NMDA receptor activation, glutamate neurotoxicity, and oxygen-glucose deprivation neuronal injury in cortical cultures. Brain Res. 506, 339–42.

Grantyn, R., and Lux, H. D. (1988). Similarity and mutual exclusion of NMDA- and proton-activated transient sodium currents in rat tectal neurons. Neurosci. Lett. 89, 198–203.

Hall, D. H., Gu, G., Garcia-Anoveros, J., Gong, L., Chalfie, M., and Driscoll, M. (1997). Neuropathology of degenerative cell death in Caenorhabditis elegans. J. Neurosci. 17, 1033–1045.

Ishibashi, K., and Marumo, F. (1998). Molecular cloning of a DEG/ENaC sodium channel cDNA from human testis. Biochem. Biophys. Res. Commun. 245, 589–593.

Kovalchuk, Y. N., Krishtal, O. A., and Nowycky, M. C. (1990). The proton-activated inward current of rat sensory neurons includes a calcium component. Neurosci. Lett. 115, 237–42.

Krishtal, O. A., and Pidoplichko, V. I. (1981). A recepotr for protons in the membrane of sensory neurons may participate in nociception. Neuroscience 6, 2599–2601.

Kristian, T., and Siesjoe, B. K. (1996). Calcium-related damage in ischemia. In Life Sci., pp. 357–367.

Leist, M., and Nicotera, P. (1999). Calcium and cell death. In Cell Death Dis. Nerv. Syst., pp. 69–90.

Li, P. A., and Siesjo, B. K. (1997). Role of hyperglycemia-related acidosis in ischemic brain damage. Acta Physiol. Scand. 161, 567–580.

Liman, E. R., Tytgat, J., and Hess, P. (1992). Subunit stoichiometry of a mammalian potassium channel determined by construction of multimeric cDNAs. Neuron 9, 861–71.

Lindahl, O. (1974). Pain—a general chemical explanation. Adv. Neurology 4, 45–47.

Lingueglia, E., De Weille, J. R., Bassilana, F., Heurteaux, C., Sakai, H., Waldmann, R., and Lazdunski, M. (1997). A modulatory subunit of acid sensing ion channels in brain and dorsal root ganglion cells. J. Biol. Chem. 272, 29778–29783.

Mattson, M. P. (1998). Free radicals, calcium, and the synaptic plasticity-cell death continuum: emerging roles of the transcription factor NFkB. In Int. Rev. Neurobiol., pp. 103–168.

Olson, T. H., Riedl, M. S., Vulchanova, L., Ortiz-Gonzalez, X. R., and Elde, R. (1998). An acid sensing ion channel (ASIC) localizes to small primary afferent neurons in rats. NeuroReport 9, 1109–1113.

Price, M. P., Snyder, P. M., and Welsh, M. J. (1996). Cloning and expression of a novel human brain Na+ channel. J. Biol. Chem. 271, 7879–82.

Reeh, P. W., and Steen, K. H. (1996). Tissue acidosis in nociception and pain. In Prog. Brain Res., pp. 143–151.

Sattler, R., and Tymianski, M. (1998). Calcium and cellular death. In Integr. Aspects Calcium Signalling, pp. 267–290.

Seguela, P., and Babinski, K. (1999). cDNA encoding human proton-gated ion channel ASIC3 and uses in screening for channel ligands. In PCT Int. Appl. (Wo: (McGill University, Can.).), pp. 32 pp.

Siesjo, B. K., Katsura, K., Mellergard, P., Ekholm, A., Lundgren, J., and Smith, M.-L. (1993). acidosis related brain damage. Progress Brain Research 96, 23–48.

Sontheimer, H., Perouansky, M., Hoppe, D., Lux, H. D., Grantyn, R., and Kettenmann, H. (1989). Glial cells of the oligodendrocyte lineage express proton-activated sodium channels. J. Neurosci. Res. 24, 496–500.

Steen, K. H., Issberner, U., and Reeh, P. W. (1995). Pain due to experimental acidosis in human skin: evidence for non-adapting nociceptor excitation. Neurosci. Lett. 199, 29–32.

Tang, C. M., Dichter, M., and Morad, M. (1990). Modulation of the N-methyl-D-aspartate channel by extracellular hydrogen ion. Proc. Natl. Acad. Sci. U. S. A. 87, 6445–9.

Tominaga, M., Caterina, M. J., Rosen, T. A., and Julius, D. (1999). The capsaicin receptor. A heat- and proton-activated ion channel. In Seibutsu Butsuri, pp. 159–164.

Ueno, S., Nakaye, T., and Akaike, N. (1992). Proton-induced sodium current in freshly dissociated hypothalamic neurones of the rat. J. Physiology (London) 447, 309–327.

Varming, T. (1999). Proton-gated ion channels in cultured mouse cortical neurons. Neuropharmacology 38, 1875–1881.

Vyklicky, L., Jr., Vlachova, V., and Krusek, J. (1990). The effect of external pH changes on responses to excitatory amino acids in mouse hippocampal neurons. J. Physiol. (London) 430, 497–517.

Waldmann, R., Bassilana, F., De Weille, J., Champigny, G., Heurteaux, C., and Lazdunski, M. (1997). Molecular cloning of a non-inactivating proton-gated Na+ channel specific for sensory neurons. J. Biol. Chem. 272, 20975–20978.

Waldmann, R., Champigny, G., Bassilana, F., Heurteaux, C., and Lazdunski, M. (1 997). A proton-gated cation channel involved in acid-sensing. Nature (London) 386, 173–177.

Waldmann, R., Champigny, G., Voilley, N., Lauritzen, I., and Lazdunski, M. (1996). The mammalian degenerin MDEG, an amiloride-sensitive cation channel activated by mutations causing neurodegeneration in Caenorhabditis elegans. J. Biol. Chem. 271, 10433–10436.

Waldmann, R., and Lazdunski, M. (1998). H+-gated cation channels: neuronal acid sensors in the NaC/DEG family of ion channels. In Curr. Opin. Neurobiol., pp. 418–424.

Wall, P. D., and Melzack, R. (1994). Textbook of Pain (New York: Churchill Livingstone).

Welsh, M. J., and Price, M. P. (1999). Cloning and sequencing of the novel human brain sodium channel BNCI cDNA. In U.S. (Us: (Usa).), pp. 24 pp.

Welsh, M. J., and Price, M. P. Cloning and sequencing of the novel human brain sodium channel BNCI cDNA. In U.S. (Us: (Usa).), pp. 24 pp.

What is claimed is:

1. An isolated and purified nucleic acid molecule selected from the group consisting of:
   a) a polynucleotide having a nucleotide sequence set forth in SEQ ID NO: 6;
   b) a polynucleotide having a nucleotide sequence set forth in SEQ ID NO: 7; and
   c) a polynucleotide that is complementary to the polynucleotide sequence of (a).

2. The polynucleotide of claim 1 wherein the polynucleotide is RNA.

3. The polynucleotide of claim 1 wherein the polynucleotide is DNA.

4. An expression vector comprising a recombinant polynucleotide encoding a protein comprising the amino acid sequence set forth in SEQ ID NO: 9.

5. The expression vector of claim 4, wherein the expression vector contains a cloned polynucleotide, having a nucleotide sequence selected from a group consisting of SEQ ID NO: 6 and SEQ ID NO: 7.

6. A recombinant host cell comprising the expression vector of claim 4.

7. The recombinant host cell of claim 6, wherein said expression vector comprises a nucleotide sequence selected from a group consisting of: SEQ ID NO: 6 and SEQ ID NO: 7.

8. A process for expression of Human BNaC4 protein in a recombinant host cell, comprising:
   (a) transferring the expression vector of claim 4 into suitable host cells; and
   (b) culturing the host cells of step (a) under conditions which allow expression of the Human BNaC4 protein from the expression vector.

* * * * *